Figure 1A:
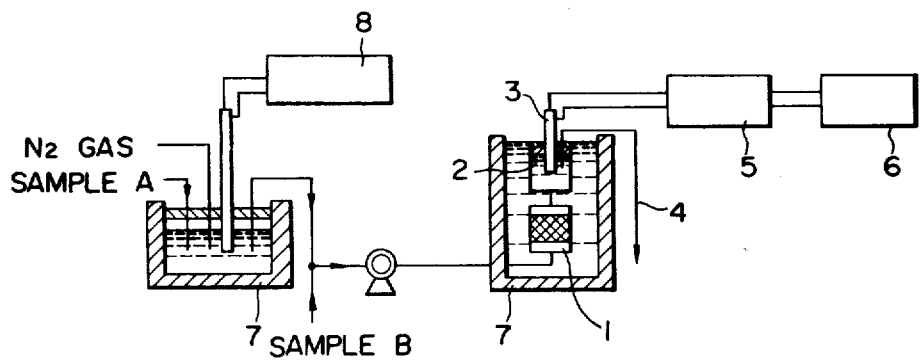

United States Patent [19]

Matsumoto et al.

[11] 4,371,612
[45] Feb. 1, 1983

[54] IMMOBILIZATION OF BIOLOGICAL MATERIAL WITH AN ACRYLONITRILE POLYMER

[75] Inventors: Kunio Matsumoto, Mishima; Rokuro Izumi, Shizuoka; Hideji Seijo, Shizuoka; Hiroyuki Mizuguchi, Shizuoka, all of Japan

[73] Assignee: Toyo Jozo Company, Ltd., Japan

[21] Appl. No.: 211,807

[22] Filed: Dec. 1, 1980

Related U.S. Application Data

[63] Continuation of Ser. No. 10,997, Feb. 9, 1979, abandoned.

[30] Foreign Application Priority Data

Feb. 17, 1978 [JP] Japan ................... 53-18001

[51] Int. Cl.[3] ............... C12P 37/06; C12N 11/08; C12N 11/06; C12P 35/00
[52] U.S. Cl. ..................... 435/44; 435/177; 435/180; 435/181; 435/288; 435/47; 435/49
[58] Field of Search ............ 435/174, 177, 180, 181, 435/288, 44, 47, 49

[56] References Cited

U.S. PATENT DOCUMENTS

| | | | |
|---|---|---|---|
| 3,705,084 | 12/1972 | Reynolds | 435/180 |
| 3,788,950 | 1/1974 | Hicks et al. | 435/181 X |
| 3,830,699 | 8/1974 | Zaborsky | 435/181 |
| 3,841,970 | 10/1974 | Matthews | 435/181 |
| 3,844,892 | 10/1974 | Matthews | 435/181 |
| 3,847,745 | 11/1974 | Axen et al. | 435/180 |
| 4,028,187 | 6/1977 | Tsutomu et al. | 435/215 |
| 4,115,305 | 9/1978 | Hornby et al. | 435/181 X |
| 4,267,273 | 5/1981 | Smith | 435/44 |

FOREIGN PATENT DOCUMENTS

| | | |
|---|---|---|
| 1226303 | 10/1966 | Fed. Rep. of Germany . |
| 2074027 | 10/1971 | France . |
| 2084750 | 12/1971 | France . |
| 2228785 | 12/1974 | France . |
| 2288748 | 5/1976 | France . |
| 1474594 | 5/1977 | United Kingdom . |

OTHER PUBLICATIONS

Inman, et al., The Immobilization of Enzymes on Nylon Structures and Their Use in Automated Analysis, Biochem. J., vol. 129, 1972, (pp. 255-262).

Sundaram et al., Preparation and Properties of Urease Chemically Attached to Nylon Tube, FEBS Letters, vol. 10, No. 5, 1970, (pp. 325-327).

Cohen et al., Reduction of Polymers Using Complex Metal Hydrides., J. Org. Chem., vol. 24, 1959, (pp. 1404-1407).

*Primary Examiner*—David M. Naff
*Attorney, Agent, or Firm*—Antonelli, Terry & Wands

[57] ABSTRACT

Biological material such as enzymes is immobilized by adsorption or covalent bonding to a micro-porous water-insoluble acrylonitrile polymer containing from 20 μM to 1000 μM of amino groups per gram of the polymer. Covalent bonding may be carried out with a crosslinking or condensing agent. The amino groups may be introduced into the polymer by reduction of nitrile groups with lithium aluminum hydride in an inert nonsolvent.

71 Claims, 10 Drawing Figures

IMMOBILIZATION OF BIOLOGICAL MATERIAL WITH AN ACRYLONITRILE POLYMER

This is a continuation of application Ser. No. 010,997, filed Feb. 9, 1979 now abandoned.

This invention relates to a novel immobilized material having a biologically active protein bound to a carrier comprising a water-insoluble acrylonitrile polymer containing amino groups and preparation thereof, to its use for specific devices and methods and also to preparation of the carrier to be used for the immobilized material.

In the prior art, polyacrylonitrile having nitrile groups has been known to have a capacity of adsorbing an enzyme which is a biologically active substance (Japanese published unexamined patent applications No. 121592/1976 and No. 7485/1977). But the amount of the enzyme adsorbed on polyacrylonitrile is small and the adsorbed enzyme will readily be released from the carrier. For this reason, polyacrylonitrile failed to be a good carrier for enzymes.

The present inventors have found that a polyacrylonitrile containing amino groups which is obtained by partial reduction of nitrile groups contained in a porous polyacrylonitrile in solid phase has unexpectedly a high adsorption capacity of enzymes, namely about 2 to 30 times as much as that of the polyacrylonitrile before treatment. The enzymes thus adsorbed on the treated polyacrylonitrile are also found to be difficultly released from the carrier. Furthermore, when an enzyme, which is a biologically active protein, is bonded to the carrier not only through physical adsorption but also when the bonding is strengthened as desired by use of a bio-condensing agent or a crosslinking agent, such as biologically active protein is immobilized with remarkable firmness onto the carrier without suffering from deactivation or deterioration. The resultant immobilized material wherein a biologically active protein is bound to the carrier is found to be active on a substrate, for which said biologically active protein shows specific activity depending on the characteristic thereof, with a long term stability and with good efficiency.

The present invention has been accomplished based on such discoveries as mentioned above, and its object is to provide an immobilized material comprising a carrier having a remarkably large amount of a biologically active protein bound thereto with good stability, a process for producing the same, its use for specific devices and methods as well as a process for producing the carrier for said immobilized material.

Figure 1B:
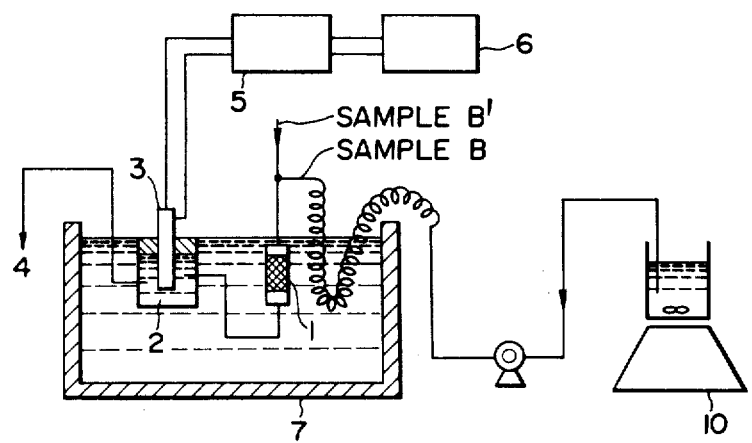
Figure 1C:
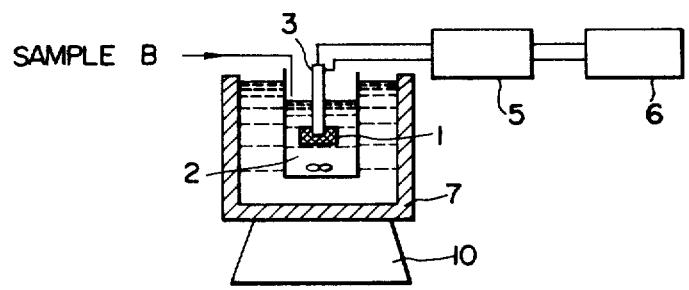
Figure 2:
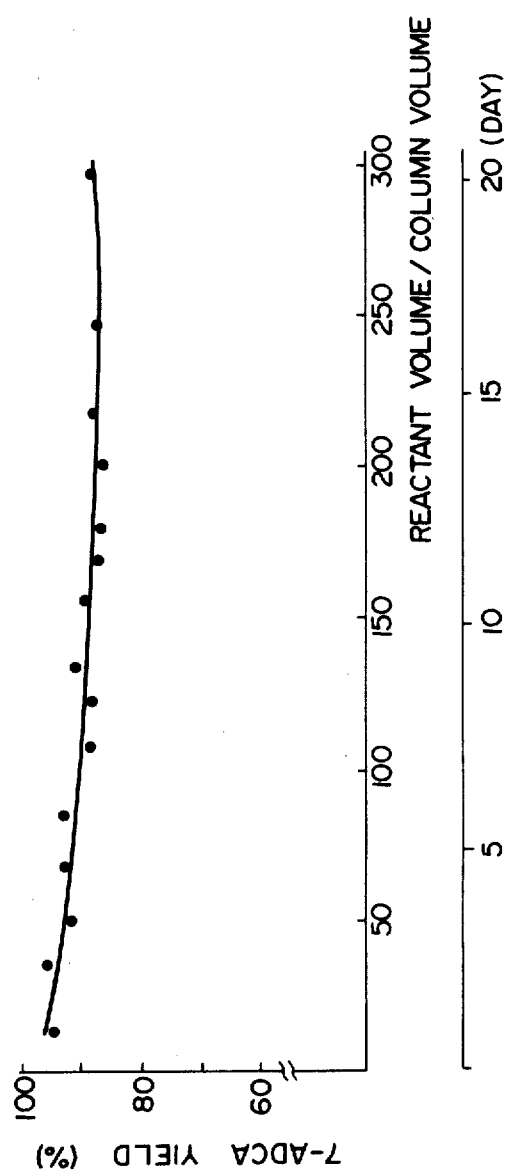
Figure 3:
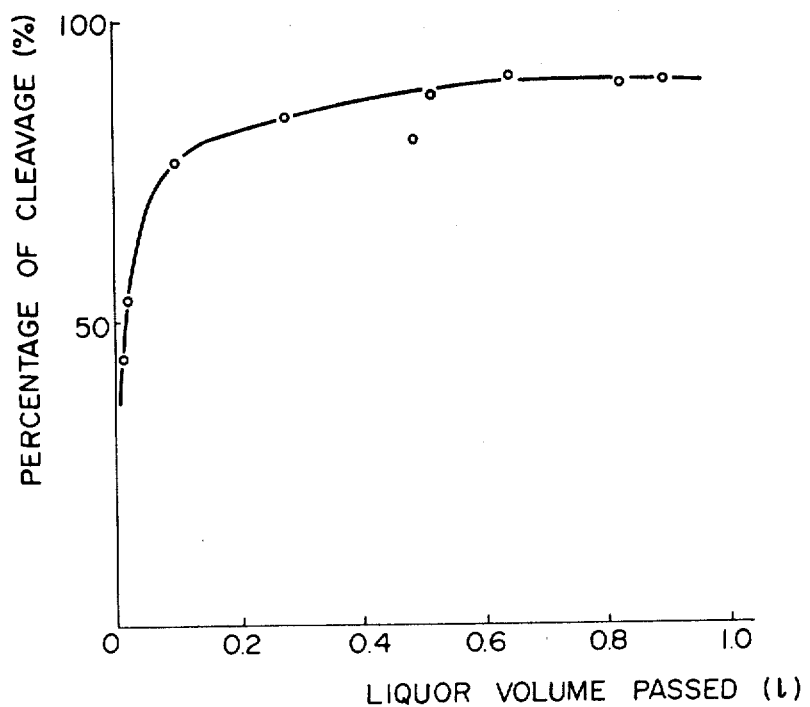
Figure 10:
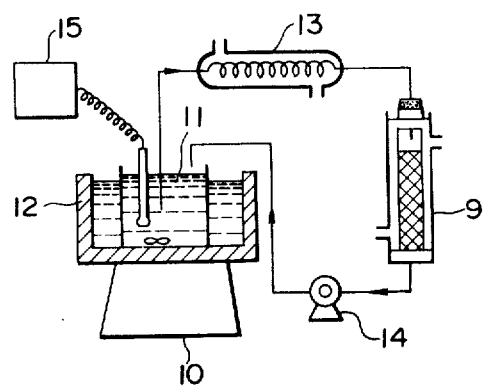
Figure 4:
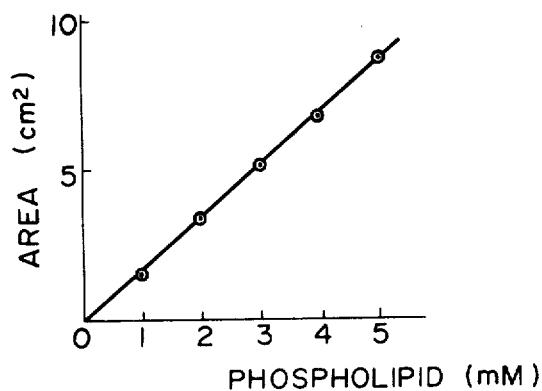
Figure 5:
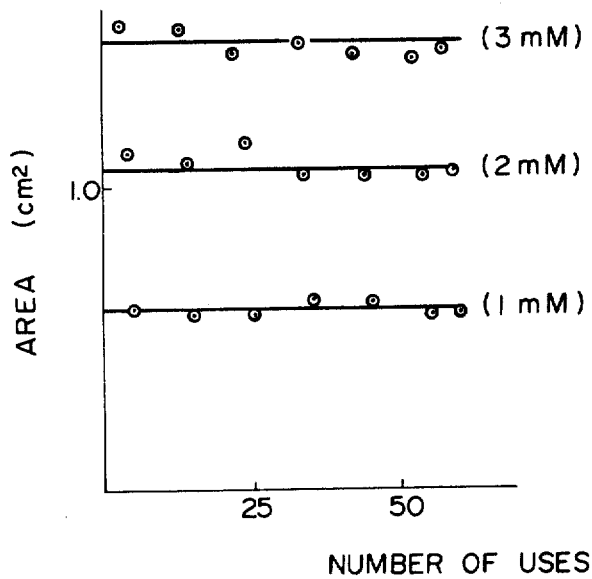
Figure 6:
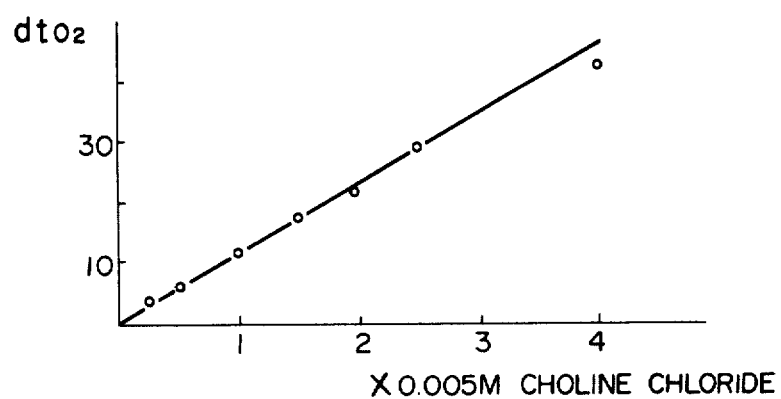
Figure 7:
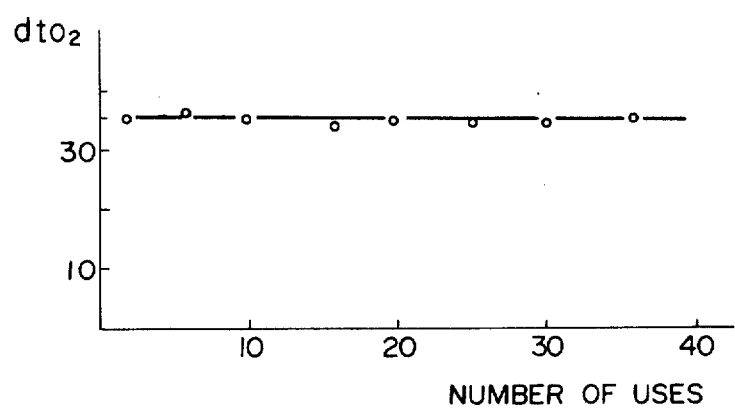
Figure 8:
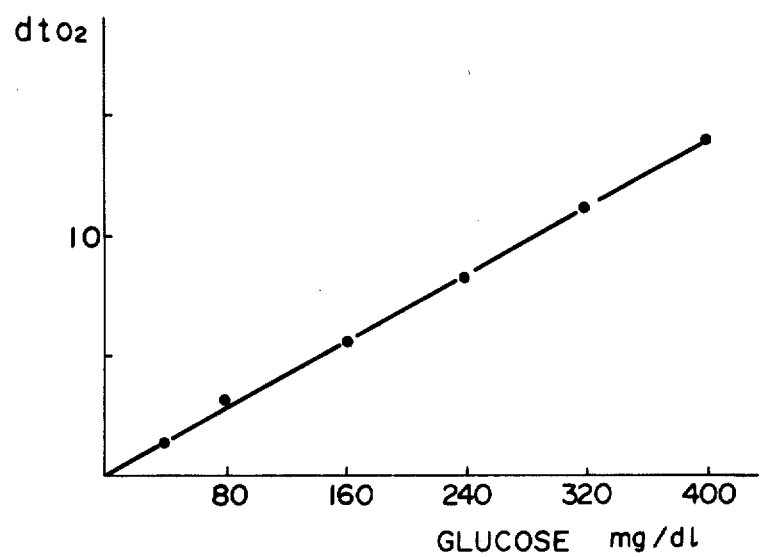
Figure 9:
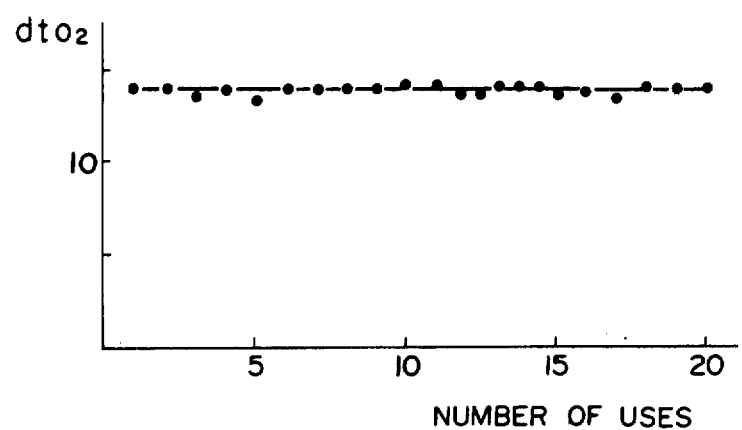

In the accompanying drawings:

FIG. 1(a) through (c) show examples of quantitative measuring device according to the present invention;

FIG. 2 a graph indicating 7-ADCA yield(%) versus reactant volume/column volume and the days for charging when there is used an immobilized material having bound the acylase produced from Bacillus megaterium B-400;

FIG. 3 a graph indicating the percentage of cleavage (yield of 7-ACA) versus the amount of the liquor passed when there is used an immobilized material having bound the acylase produced from Comamonas sp. SY-77-1;

FIG. 4 a calibration curve indicating the peak area recorded on the recorder by enzymatic reaction versus amount of the substrate when there is used an immobilized having bound in combination phospholipase D and cholineoxidase;

FIG. 5 a graph indicating stability of enzyme versus the number of repeated uses when there is used an immobilized material having bound in combination phospholipase D and cholineoxidase;

FIG. 6 a calibration curve indicating the maximum velocity differential ($dtO_2$) recorded on the recorder versus the amount of chloline chloride which is the substrate, when there is used an immobilized material having bound cholineoxidase;

FIG. 7 a graph indicating stability of enzyme versus the number of repeated uses when there is used an immobilized material having bound cholineoxidase;

FIG. 8 a calibration curve indicating the maximum velocity differential ($dtO_2$) versus the amount of glucose which is the substrate when there is used an immobilized material having bound glucoseoxidase;

FIG. 9 a graph indicating stability of the enzyme versus the number of repeated uses when there is used an immobilized material having bound glucoseoxidase; and FIG. 10 a production device comprising the immobilized material according to the present invention.

The specific feature of the present invention resides in using a specific carrier for immobilizing biologically active proteins, which is a water-insoluble acrylonitrile polymer containing amino groups.

The term "acrylonitrile polymer" herein mentioned refers to a polymer of acrylonitrile monomers such as acrylonitrile, methacrylonitrile, α-chloroacrylonitrile, cinnamnitrile, etc. or a copolymer of such monomers with other comonomers containing ethylenically unsaturated double bonds. Typical examples of such comonomers may include styrene monomers such as styrene, methyl-styrene, ethyl-styrene, nitro-styrene, chloro-styrene, bromo-styrene, chloromethyl-styrene and the like; acrylic or methacrylic acid ester monomers such as methyl (meth)acrylate, ethyl (meth)acrylate, butyl (meth)acrylate, 2-hydroxyethyl (meth)acrylate, polyethyleneglycol (meth)acrylate and the like; conjugated dienes such as butadiene, isoprene and the like; halogenated olefins such as vinyl chloride, vinylidene chloride and the like; vinyl ether monomers such as ethyl vinyl ether, butyl vinyl ether and the like; vinyl ketone monomers such as methyl vinyl ketone, ethyl isopropenyl ketone and the like; vinyl ester monomers such as vinyl acetate, vinyl benzoate and the like; amide vinyl monomers such as (meth)acrylamide, N,N-dimethyl(meth)acrylamide, N-vinyl pyrrolidone, N-vinyl succinimide N-vinyl phthalimide and the like; basic monomers such as vinyl pyridine, methyl vinyl pyridine, vinyl imidazole, N,N-diethylaminoethyl (meth)acrylate and the like; polyfunctional monomers such as divinyl benzene, divinyl toluene and the like; and others. These comonomers may be copolymerized with the acrylonitrile monomers, optionally in the presence of a crosslinking agent such as divinyl benzene, divinyl toluene, etc.

In preparation of the aforesaid carrier, the acrylonitrile polymer is desired to be porous in nature in order to impart good characteristics thereto. For the purpose of obtaining a porous structure, for example, acrylonitrile together with other monomers, if desired, may be subjected to suspension polymerization or emulsion polymerization in an aqueous system. Alternatively, said polymer is dissolved in a soluble solvent such as dimethylformamide, dimethylsulfoxide, conc. nitric acid, an aqueous rhodanate solution, an aqueous zinc chloride solution, etc. and then the resultant solution is added dropwise or extruded in the shape of filaments or membranes into a coagulation bath containing water, an aqueous acetone solution, an aqueous ethanol solution, an aqueous dimethylformamide solution, etc. to be formed into particles, fibers or membranes. Furthermore, it is also possible to form the polymer in the shape of hollow filaments. The thus obtained porous structure is presumably considered to have macro-voids which permit biologically active proteins to permeate into inner portions thereof and micro-pores which trap biologically active proteins on the surface or in inner portions thereof. Through such micro-pores, the biologically active proteins are considered to be attached to the carrier. These micro-pores have sizes distributed generally in the range from about 40 to 9000 Å, preferably about 50 to 4000 Å, most typically about 100 to 2000 Å.

As the next step, free amino groups are introduced into the acrylonitrile polymer as described above to give the acrylonitrile polymer containing amino groups, namely the carrier according to the present invention. Since immobilization of biologically active proteins is conducted in an aqueous medium, introduction of amino groups should be effected so as to give a water-insoluble carrier. As such methods, there may be employed various reactions well known in the art. For example, nitrile groups in the acrylonitrile polymer may be reduced to be converted to amino groups. When said polymer is previously endowed with porous structure, such reduction may preferably conducted in an inert non-solvent which does not dissolve said polymer in order to avoid disintegration of the porous structure. As preferable reducing agent for such reduction reactions, there may be employed, for example, lithium aluminum hydride. Since the above reduction reaction is carried out in solid phase, the acrylonitrile polymer employed is desired to be previously endowed with porous structure. As an inert non-solvent, there may be used organic solvents such as diethyl ether, dioxane, tetrahydrofuran, etc. The above reaction may be conducted at room temperature or at around boiling point of the non-solvent employed. The reaction time, which may vary depending on the polymer employed, its shape, its structure or its polymerization degree, may suitably within 10 minutes to 48 hours. As the result of the above reaction, nitrile groups in said polymer are partially converted by reduction to amino groups. The reduction reaction is continued until the carrier is aminated to an extent having at least 20 μM of amino groups per gram of the carrier but before said carrier is substantially soluble in water. Usually, the aminated carrier contains 20 to 1000 μM of amino groups per gram of carrier. It seems that the amino groups are more dense on the surface of the polymer than in the inner portion thereof. The thus obtained carrier may be subjected, if desired, to washing with water, with an acidic aqueous solution or with an alkaline aqueous solution.

As another method for reducing nitrile groups to amino groups, there may also be employed catalytic reduction of an acrylonitrile polymer in an autoclave in the presence of an organic solvent which can dissolve said polymer. But, according to this reaction, amination may proceed to such an extent as rendering the product soluble in water. Furthermore, this method required the step for making the polymer porous. For these reasons, this method is not an advantageous one.

According to still another method for obtaining an acrylonitrile polymer having amino groups, ammonia is allowed to react with an acrylonitrile polymer having halogenic atomic groups, especially chlorine atom groups, to substitute chlorine atom groups with free amino groups. Alternatively, an acrylonitrile polymer containing epoxy groups may be reacted with lysine, an alkylene diamine such as hexamethylene diamine, dodecamethylene diamine, etc. Said polymer can also be obtained by subjecting a copolymer of an acrylonitrile monomer with an amide type vinyl monomer, namely an acrylonitrile polymer having amide groups to Hoffman degradation. Still another method comprises reducing nitro groups of an acrylonitrile polymer containing nitro groups, which is obtained by nitration in conc. nitric acid-sulfuric acid mixture of a copolymer of an aromatic vinyl monomer such as a styrene monomer, divinyl benzene or vinyl ethyl benzene with an acrylonitrile monomer when said copolymer has no nitro group, with sodium hydrosulfite-potassium hydroxide solution. Furthermore, it is also possible to obtain said polymer by subjecting a copolymer of an acrylonitrile monomer with methyl vinyl ketone to ammonia treatment.

The thus prepared acrylonitrile polymer containing amino groups may be subjected, prior to binding with a biologically active protein if desired, to treatment with a crosslinking agent such as glutaraldehyde in an inert medium such as an aqueous medium preferably with cooling for prevention of polymerization of glutaraldehyde, followed further by treatment with a compound as spacer such as hexamethylene diamine, dodecamethylene diamine or other alkylene diamines, or lysine similarly in an aqueous medium at 0° C. to room temperature, and thereafter subjected again to treatment with a crosslinking agent to give the objective carrier.

The carrier obtained according to the procedure as described above may preferably have a porous structure and is shaped in fibers, particles, membranes or hollow filaments. This porous structure is presumably considered to have macro-voids which permit biologically active proteins to permeate into inner portions thereof and micro-pores which trap biologically active proteins on the surface or in inner portions thereof. The size of the micro-pores are generally from 40 to 9000 Å, preferably about 50 to 4000 Å, more preferably about 100 to 2000 Å.

As the next, step the above carrier which is preferably of a porous structure is combined with a biologically active protein. Typical examples of biologically active protein are various enzymes. They include oxidoreductases, hydrolases, transferases, lyases, isomerases, ligases, etc. Examples of oxidoreductases are alcohol dehydrogenase, glycerol dehydrogenase, glycerol phosphate dehydrogenase, lactate dehydrogenase, galactose dehydrogenase, glucose-6-phosphate dehydrogenase, 3-hydroxybutyrate dehydrogenase, glucoseoxidase, cholesteroloxidase, galactoseoxidase, chlolineoxidase, pyruvic acid oxidase, glutamic acid dehydrogenase, amino acid oxidase, amine oxidase, sarcosine oxidase, diaphorase, uricase, peroxidase, catalase, lipoxygenase, etc. Examples of hydrolase are lipase, phospholipase, acetylchlolineesterase, cholesterolesterase, phosphatase, amilase, glucosidase, galactosidase, pepsin, trypsin, chymotrypsin, papaine, bromelein, urease, aminoacylase, penicillin acylase, cephalosporin acylase, penicillinase, cephalosporinase, creatinase, creatininase, etc. Examples of transferases are creatin phosphokinase, pyruvate kinase, hexokinase, glycerol kinase, etc. Examples of isomerases are alanine isomerase, glucose isomerase, glucose phosphate isomerase, etc. Typical example of ligase is glutathione synthetase. In addition to the enzymes as set forth above, there may be used any biologically active protein which can be bound to the carrier. For example, there may be used hormones, antigens and antibodies. These biologically active proteins may be used singly or as a combination of two or more species.

The biologically active protein can be attached to the above carrier by physical adsorption or covalent bonding method (carrier crosslinking method). For such bonding methods, there may be applied suitably the bonding methods for attaching enzymes to carriers having free amino groups well known in the art, as described in "IMMOBILIZED ENZYMES" (edited by Ichiro Chibata, published by Kodansha Co., Ltd., Japan).

For example, the attachment method by physical adsorption may be conducted either by the column process in which the carrier is packed in a column or by the batch process in which the carrier is dispersed in a vessel. As an inert medium to be used in this method, there may be employed any medium which does not deactivate the biologically active protein used, preferably an aqueous medium such as water, buffer solutions adjusted at various pH (e.g. acetate buffer of pH 4 to 6, phosphate buffer of pH 6 to 8, borate buffer of pH 8 to 9, etc.). The bonding is performed at a temperature at which the biologically active protein is not activated, usually at 0° to 30° C. The amount of the biologically active protein used may be as much as saturation of the bonding capacity of the carrier. The quantity adsorbed on the carrier is judged by the presence or absence of the activity of the biologically active protein in the inert medium or by subjecting the immobilized material to biological activity assay. Thus, the amount of the biologically active protein attached to the carrier may suitably be controlled depending on the activity of the biologically active protein used.

The bonding between the carrier and the biologically active protein may also be conducted by covalent bonding method. According to this method, immobilization is effected by use of a bonding agent in the same or different system. As the bonding agents, there may be employed which effect bonding by utilizing amino groups in the carrier and free groups in the biologically active protein such as amino groups, carboxylic groups or hydroxyl groups. For example, there may be employed crosslinking agents such as hexamethylene diisocyanate, hexamethylene diisothiocyanate, toluene diisocyanate, xylene diisocyanate, glutaraldehyde, dialdehyde starch, dimethyl adipimidate, dimethyl suberimidate, dimethyl-3,3'-dithiobispropionimidate, succinic acid anhydride, croton aldehyde, acrolein, etc., whereby said carrier is bonded to the biologically active protein directly or through intermediary spacer such as lysine, hexamethylene diamine, etc. When the carrier and the biologically active protein are directly attached by covalent bonding, water-soluble condensing agent such as 1-ethyl-3-(3-dimethylaminopropyl)-carbodiimide are used. The bonding reaction by using such a bonding agent as set forth above is carried out in an inert medium, for example, an aqueous medium which may contain tetrahydrofuran, acetone, ethanol, etc. Said reaction may be conducted preferably at room temperature and at pH at which the biologically active protein can be stable, generally in the range from 4 to 12. The bonding agent may be used in an amount of once to twice as much as the moles of the free groups to be bonded.

The immobilized material prepared according to the above procedure has a noticeably good activity of the biologically active protein and is useful for various purposes depending on the specific charcteristics of the biologically active protein used. Accordingly, by providing a system of the immobilized material and a system containing a substance sensitive to the activity of the biologically active protein, for example, a substrate in case when it is an enzyme, optionally in the presence of a buffer solution for maintaining the pH optimum for the enzyme, it is possible to perform collection of the enzymatic reaction product and quantitative analysis of the substrate by utilization of the enzymatic reaction.

The substrates to be used in the present invention may be in various states, including aqueous solutions, aqueous mediums (e.g. buffer solutions) and those of body fluids such as blood, urine or treated liquids thereof. For example, when an acylase is to be employed as enzyme, the substrate may be a solution of a 7-acyl-cephalosporanic acid derivative, a solution of 6-acyl-penicillanic acid derivative or a solution of 7-amino-3-cephem-4-carboxylic acid or its derivative, or 6-amino-penam-3-carboxylic acid or its derivative and methyl thienyl acetate or methyl α-aminophenyl acetate. On the other hand, when cholineoxidase, various phospholipase, uricase or glucoseoxidase is to be employed, there may be used as substrate corresponding phospholipids, uric acid, glucose, body fluids such as blood or urine.

When penicillin acylase as produced from *Bacillus megaterium* B-400 (FERM-P 748) *Escherichia coli* ATCC 9637, *Escherichia coli* ATCC 11105 or others is immobilized by use of the above carrier, there can be obtained an immobilized penicillin acylase having extremely high specific activity. By using said immobilized penicillin acylase, when natural penicillin solution with a high concentration of 3 to 12 W/V % is used as substrate, there can be obtained 6-APA in a high yield of 95% or more. The resultant 6-APA can be recovered at high purity and high yield by merely adjusting the pH of the reaction mixture at the isoelectric point of 6-APA without performing concentration operation of the reaction mixture. The above immobilized penicillin acylase can be used repeatedly for many times for a long time and therefore the cost of said immobilized enzyme involved in the production cost of 6-APA is almost negligible. Furthermore, the immobilized enzyme can be applicable not only in the stage, wherein penicillin is isolated by purification in the form of salt from penicillin fermented broth but also for the extracted solution obtained by phase transfer of penicillin into an aqueous solution, whereby it is made possible to produce 6-APA at further reduced cost. The immobilized enzyme of the present invention has various advantages as mentioned above.

The present invention also provides a specific device and method in which the immobilized material as described above is utilized. Such a device comprises a combination of a system containing an immobilized material having bound an enzyme to said carrier, a system containing a substrate on which said enzyme has activity and a system for detecting the change in the enzymatic reaction in said systems. Referring now to the accompanying drawings, preferred embodiments of the devices and the methods of the present invention are described below.

In the device as shown in FIG. 1(a), said immobilized material is packed in column 1 to provide a reaction vessel. At measuring means 2 connected by means of glass tube to the reaction vessel comprising the system having the immobilized material, there is set electrode 3, for example, glass electrode, oxygen electrode, etc. The volumes of the reaction vessel and the measuring means 2 are made as small as possible so as to make smaller the errors by diffusion of the reaction mixture. The electrode 3 is connected, if necessary, to electrometer or dissolved oxygen meter 5 provided with differential converter, said meter being further connected to the recorder 6. In quantitative determination, a sample or reference liquid previously adjusted at constant pH is charged into the reaction vessel from the sample inlet to cause electric change (potential change, dissolved oxygen change) corresponding to the substrate concentration through enzymatic reaction. The sample concentration is quantitatively determined from the potential value and the calibration curve. When a glass electrode is used in quantitative determination, nitrogen gas is introduced into the reaction vessel. This is because pH change is caused by the carbon dioxide in the air (similarly as in the electrode 3) if the air is introduced into the reaction vessel. The pH meter 8 is provided for the purpose of correction of the difference in pH between the sample solution and the reference solution.

The inlet for charging samples may be the same as that for charging the reference solution. In this case, the same inlet is used alternately for these purposes. When separate inlets are to be provided, inlets each having the same function may be provided at different positions. The inlets for charging may be provided on the device at two positions.

The thermostat bath 7 may be adjusted at a temperature which can permit the enzymatic reaction to proceed, preferably at 30° to 70° C. and the reaction is continued for a time necessary for the enzymatic reaction.

The quantitative determination method may be performed either by batch process or continuous process.

The amount of the sample charged has an influence on the activity of the enzyme used, but there is used usually 1 to 2 ml/min. of a sample in continuous process so as to permit the substrate in the sample to undergo favorable reaction. The sample concentration, which will vary depending on the activity of the enzyme used, may be diluted to any concentration when it is too high.

The reaction product produced by the enzymatic reaction in the various devices may be isolated and recovered by conventional procedures. Furthermore, when the quantitative determination as described above is simultaneously conducted, the sample concentration or the quantity of the sample can be determined depending on the intended purposes.

In the aforesaid quantitative measuring device, when the electrode 3 is an oxygen electrode, pH meter 8 is not necessarily used but recording by means of recorder through differential converter may also be effected. Such a combination may optionally be changed; the devices as shown in FIG. 1(b), 1(c) and FIG. 10 can also be used.

Referring to the system of fluids containing phospholipids, choline, betaine aldehyde as contained in body fluids, such a system may preferably combined with a system containing an immobilized material having bound cholineoxidase on a carrier alone or together with phospholipase D which is untreated or bound on said carrier, optionally with indicators or buffer solutions, and also with auxiliary equipments. In such a combination of systems, these immobilized materials and said fluids are subjected to incubation for a certain time, whereby hydrogen peroxide and betaine are formed from the enzymatic reaction to effect reduction in oxygen. Subsequently, the hydrogen peroxide, betaine and oxygen formed from this reaction are measured. In measurement of oxygen, an oxygen electrode may most conveniently be used; in measurement of betaine, Reineckes salt method is preferred or betaine may be esterified, followed by gas chromatographic analysis. In measurement of hydrogen peroxide, hydrogen peroxide may preferably be measured by a meter using a hydrogen peroxide electrode (e.g. oxidase meter produced by YSI Co.) in the same apparatus as described above; alternatively it may be measured by colorimetric measurement using a system comprising one or two or more kinds of indicators which will cause change in color tone with reaction of the hydrogen peroxide. Typical examples of such measurement methods are one in which there is used the reaction of the hydrogen peroxide formed with tetravalent titanium compound and xylenol orange, thereby forming stable red color, and one in which there is used the reaction with phenol, 4-amino antipyrine and peroxidase. In the latter method for measurement of hydrogen peroxide, wherein the reaction with phenol, 4-amino antipyrine and peroxidase is utilized, 4-amino antipyrine is used desirably in an amount of at least $\frac{1}{2}$ mole preferably 2 moles or more per mole of the hydrogen peroxide formed; while the amount of peroxidase used being at least 0.1 U, preferably about 0.2 to 0.5 U. Furthermore, 4-amino phenazone may also be used. Each of these reagents may be prepared by previously mixing into a solution. The thus indicated color tone is measured at suitable wavelength and the hydrogen peroxide present in the system is quantitatively determined according to calibration curve, whereby quantitative determinations can be made of the existing choline or betaine aldehyde or derivatives of choline or derivatives of betaine aldehyde, and also of the activity of the enzyme which hydrolyzes choline derivatives. Other than the methods as mentioned above, there may be used quantitative measurement of hydrogen peroxide by use of a combination of 2,6-dichlorophenol indophenol and peroxidase, quantitative measurement of hydrogen peroxide by use of guayac fat and peroxidase, quantitative measurement of hydrogen peroxide by use of a combination of homovanilic acid and peroxidase or other various methods. In the various devices and methods as described above, the immobilized material of the present invention may be used in various shapes such as particles, filaments or membranes.

The present invention is further illustrated by the following Examples and Reference examples, by which the present invention is not limited.

In the following Examples and Reference examples, the activity assay when an enzyme is used as biologically active protein is conducted according to the methods as explained below.

PENICILLINACYLASE ACTIVITY ASSAY (1) Enzyme solution

The reaction mixture comprising 0.5 ml of an enzyme solution, 4.0 ml of 0.1 M phosphate buffer (pH 7.5), and 0.5 ml of 4(W/V)% PcG potassium salt/0.1 M phosphate buffer (pH 7.5) is allowed to react at 37° C. for 30 minutes. A sample (0.5 ml) from the reaction mixture is added to 3 ml of a buffer comprising 1 ml of 0.05 N sodium hydroxide and 2 ml of 20% acetic acid with 0.5 ml of 0.5 (W/V)% P-dimethylaminobenzaldehyde/methanol solution. The resultant mixture is allowed to react at room temperature for 10 minutes. By measurement of absorption at 415 nm, the amount of 6-APA formed is determined.

The enzyme activity which produces 1µ mole of 6-APA per one minutes is defined as one unit (1 U).

(2) Immobilized enzyme

A previously weighed immobilized enzyme is added to a solution comprising 4.5 ml of 0.1 M phosphate buffer (pH 7.5) and 0.5 ml of 4(W/V)% PcG potassium salt/0.1 M phosphate buffer (pH 7.5) and the reaction is carried out at 37° C. for 30 minutes. The amount of 6-APA formed is determined similarly as in case of the enzyme solution.

ACYLASE ASSAY 1

A system comprising 0.25 ml of an acylase containing liquid and 0.25 ml of a solution containing 1% 7-(4-carboxybutaneamido)-desacetoxy cephalosporanic acid as substrate in 0.1 M phosphate buffer (pH 7.0) or a system comprising an immobilized material having acylase bound to a carrier, 2.0 ml of the same substrate solution as mentioned above and 2.0 ml of 0.1 M phosphate buffer is subjected to the reaction at 37° C. for 30 minutes. To 0.5 ml of the reaction mixture containing 7-amino-desacetoxy cephalosporanic acid (7-ADCA) formed after the reaction are added 3 ml of a buffer comprising 1 ml of 0.05 N sodium hydroxide and 2 ml of a 2.0% acetic acid and 0.5 ml of a 0.5% p-dimethylaminobenzaldehyde methanol solution. The mixture is allowed to react at room temperature for 10 minutes. The product is subjected to measurement of absorption at 415 nm. The amount of 7-ADCA in sample is calculated from the calibration curve of 7-ADCA. The activity which produces 100 γ/ml of 7-ADCA is defined as 100 U.

This measurement method is conducted by utilizing the acylase produced from Comamonas sp. SY-77-1(FERM-P 2410).

ACYLASE ASSAY 2

In place of the substrate used in the above acylase assay-1, there is used 0.1 M phosphate buffer (pH 7.5) containing 1% 7-phenylacetamidodesacetoxy cephalosporanic acid under otherwise the same conditions as in the acylase assay-1. In this assay, there is used the acylase produced from *Bacillus megaterium* B-400(FERM-P 748).

CHOLINEOXIDASE ACTIVITY ASSAY

A system comprising 5 µl of a cholineoxidase containing solution or 1 to 5 mg of an immobilized material having cholineoxidase bound to a carrier, 0.05 ml of 0.2 M tris-hydrochloride buffer (pH 8.0), 0.05 ml of 3 mg/ml 4-aminoantipyrin, 0.10 ml of 0.1% phenol, 0.10 ml of 2 U/mg peroxidase, 0.10 ml of 0.1 M choline chloride and 0.1 ml of distilled water is subjected to the reaction at 37° C. for 5 minutes. The reaction is terminated with addition of 2.5 ml of ethanol. Absorption is measured at 480 nm. The activity which produces 1µ mole of hydrogen peroxide per one minute is defined as 1 U. The activity of said immobilized material is calculated according to the following formula:

$$\text{Activity }(U/g) = \frac{\Delta A 480 \text{ nm} \times 0.35 \times 1000}{\text{reaction time (min.)} \times \text{immobilized material (mg)}}$$

In the above assay, there is used cholineoxidase which is produced from *Arthrobacter globiformis* B-0577.

PHOSPHOLIPASE D ACTIVITY ASSAY

A system comprising 0.05 ml of a phospholipase D containing solution, 0.1 ml of 0.2 M tris-hydrochloride buffer (pH 8.0), 0.1 ml of 10 mM lecithin emulsion, 0.05 ml of 0.1 M calcium chloride, 0.1 ml of 1% Triton X-100 and 0.1 ml of water is subjected to the reaction at 37° C. for 10 minutes. Alternatively, a system comprising 1 to 5 mg of an immobilized material having bound phospholipase D to a carrier, 0.15 ml of 0.2 M tris-hydrochloride buffer (pH 8.0), 0.1 ml of 10 mM lecithin emulsion, 0.05 ml of 0.1 M calcium chloride, 0.1 ml of 1% Triton X-100 and 0.1 ml of water is subjected to the reaction at 37° C. for 5 minutes. The reaction is then terminated by boiling the system, followed by cooling to 37° C. To the reaction mixture are added 0.1 ml of 4-aminoantipyrine (3 mg/ml), 0.1 ml of 2 U/ml peroxidase, 0.10 ml of 0.1% phenol, 0.1 ml of 12 U/ml cholineoxidase and 0.1 ml of water. The resultant mixture is subjected to the reaction at 37° C. for 20 minutes. After addition of 2 ml of 1% Triton X-100 to the reaction mixture, absorption is measured at 500 nm. The activity producing 1µ mole of choline per one minute is determined as 1 U. The activity of said immobilized material is calculated according to the following formula:

$$\text{Activity }(U/g) = \frac{\Delta A 500 \text{ nm} \times 0.25 \times 1000}{\text{Reaction time (min.)} \times \text{material (mg)}}$$

In this method, there is utilized phospholipase D.

The various methods for assay of enzyme activities as described are only examples and other known methods may be used. It is also possible to use other methods suitable for the enzymes utilized. In case when the utilized enzyme is the immobilized enzyme according to the present invention, it can be provided as enzyme electrode with attachment of reaction vessel and measuring means to assemble an device, and in said reaction vessel there may be employed a system comprising a suitable combination of various reagents corresponding to the enzyme utilized and solutions containing corresponding substrate as sample and reference to carry out the measurement according to the methods as described above.

EXAMPLE 1

Preparation of polyacrylonitrile having porous structure

A three-necked flask of 500 ml capacity is immersed in a thermostat water-bath maintained at about 35° C. and replaced with nitrogen for about 15 minutes. Then, into the flask is charged 120 ml of distilled water, followed further by addition of 2 g of sodium alkylsulfonate, 80 g of acrylonitrile, 0.1 g of sodium persulfate and 0.033 g of hydrous sodium sulfite. After stirring the mixture for about 3 hours, there is obtained an emulsion. The emulsion is poured into about 500 ml of water and sodium chloride is added thereto to effect precipitation of the product by coagulation. The precipitates are separated by filtration, washed with water and dried on air to give polyacrylonitrile having an inherent viscosity of about 10.5 (as measured in 0.5% dimethylformamide solution at 30° C.).

Then, 10 g of this polyacrylonitrile is dissolved in 150 ml of dimethylformamide and the resultant solution is extruded in the form of filaments into a 20% aqueous dimethylformamide solution to prepare filaments (thickness: 20 to 35 microns) of polyacrylonitrile (containing 90% or more of acrylonitrile) having a porous structure.

The same polyacrylonitrile solution is added dropwise by an atomizer cup into a 20% aqueous dimethylformamide solution, whereby there are obtained particles of polyacrylonitrile having a porous structure (average particle diameter: 100 mesh).

EXAMPLE 2

Preparation of aminated polyacrylonitrile

To 1.5 g of lithium aluminum hydride is added 120 ml of dry diethyl ether. The porous polyacrylonitrile fiber (containing 90% or more of acrylonitrile), 1.5 g obtained in Example 1 is added to the resultant solution. With equipment of a reflux condenser, the mixture is subjected to heating under reflux in an oil bath at 50° C. for 10 minutes to 30 hours. After the reaction, the fibers are taken out, washed with dry diethyl ether, followed by thorough washing with 1 N hydrochloric acid, water, 1 N aqueous sodium hydroxide solution and water, successively, to give aminated polyacrylonitrile fibers (thickness: 20 to 35 microns). The unaltered lithium aluminum hydrochloride is decomposed by dropwise addition of a small quantity of water.

The aminated polyacrylonitrile fibers obtained have the following physical properties:

Color: slightly more colored in yellow than polyacrylonitrile, yellowish color being intensified as the reduction time is prolonged;

Viscosity: unmeasurable because not soluble in the solvents as set forth below;

Solubility in various solvents:

|  | Aminated polyacrylonitrile fibers; | Polyacrylonitrile fibers |
|---|---|---|
| DMSO (dimethylsulfoxide) | partly soluble* | soluble |
| DMF (dimethylformamide) | " | " |
| conc. nitric acid | " | " |
| 65% KSCN solution | " | " |
| chloroform | insoluble | insoluble |
| acetonitrile | " | " |
| pyridine | " | " |
| nitromethane | " | " |
| cyclohexane | " | " |
| diethyl ether | " | " |
| dioxane | " | " |
| tetrahydrofuran | " | " |
| 30% aqueous NaOH solution | " | " |

*not completely dissolved, while remaining the thickness of fibers without substantial change; partial solubility is detected by turbidity of the solvent by addition of water as well as from the loss in weight as shown in the following experiment.

Various aminated polyacrylonitrile fibers, each 30 mg, obtained after various reduction time are added into 5 ml of dimethylformamide and each mixture is subjected to heat treatment at 60° C. for 3 minutes. Then, the fibers are separated by filtration, washed with water and dried. The weight of the fibers after drying is measured to give the results as set forth below:

| Reduction time | Loss in weight (%) |
|---|---|
| 5 minutes | 31.3 |
| 1 hour | 29.0 |
| 5 hours | 27.0 |

Color indication by sodium 2,4,6-trinitrobenzene sulfonate is not recognized for polyacrylonitrile fibers, but the aminated polyacrylonitrile fibers are found to indicate yellow color, whereby the presence of amino groups can be confirmed.

Content of amino groups: The results of measurement of the immobilized protein and the estimated content of amino groups on the carrier as determined from the following test methods are shown in Tables 1 to 3.

(1) Immobilized enzyme

Various carriers as obtained above after various reaction time, each 18 mg, are added into 10 ml of 12.5% glutaraldehyde/borate buffer (pH 8.5) and each mixture is stirred at 0° C. for 20 minutes. The fibers are separated by filtration and thoroughly washed with borate buffer (pH 8.5) and 0.1 M phosphate buffer (pH 7.5). Immediately thereafter, the fibers are added into 2 ml of 0.3% bovine serum alubumin or penicillinacylase (140 U/ml) of *Bacillus megaterium* B-400/0.1 M phosphate buffer (pH 7.5), and the mixture is subjected to shaking at 30° C. for one hour. After filtration, bovine serum alubumin and penicillinacylase remained in the mother liquor are quantitatively measured by Lowry method [(O. H. Lowry, J. Biol. Chem., 193, 265(1951)] to determine the content of bovine serum alubumin or penicillinacylase bound onto said carrier.

Said carrier, without treatment with glutaraldehyde, is also directly added into the bovine serum alubumin solution or the penicillinacylase solution, followed by shaking at 30° C. for one hour, determine the amount of bovine serum alubumin or penicillinacylase adsorbed on said carrier according to the procedure as described above.

(2) Estimated content of amino groups by amino acid attachment

Each of various carriers (18 mg) as obtained above after various reaction time is similarly treated in (1) with 12.5% glutaraldehyde solution, and thereafter added into 2 ml of a 0.1 M phosphate buffer (pH 7.5) containing 0.3% each of glutamic acid (Glu), threonine (Thr) or 7-amino desacetoxy cephalosporanic acid (7-ADCA), followed by shaking at 30° C. for one hour. The reaction mixture is separated by filtration and the amino acid content in the supernatant is quantitatively determined by automatic amino acid analyzer, from which the amino acid content in said carrier is determined as the amino acid binding capacity. In practicing this experiment, the absence of adsorption capacity of the amino acids employed on said carrier is confirmed by the experiment in which amino acid hydrazide is used in place of amino acid. When 7-ADCA is employed as the amino acid, the content in the supernatant is determined by means of high speed liquid chromatography from the absorption in the ultraviolet region at 254 nm to determine 7-ADCA binding capacity of the carrier.

(3) Estimated content of amino groups by titration

Each of various carriers obtained after various reduction time (80 mg) is stirred together with 15 ml of a 2 mM hydrochloric acid and 30 ml of distilled water for one hour. The excessive hydrochloric acid is titrated with 2 mM aqueous sodium hydroxide solution to determined the amount of the hydrochloric acid consumed as hydrochloride corresponding to the content of amino groups in the sample carrier.

TABLE 1

| Reflux time (hours) | Amount of bound protein | | | |
|---|---|---|---|---|
| | Bovine serum alubumin γ/mg | | Penicillinacylase γ/mg | |
| | Glutaraldehyde treatment | Adsorption with no treatment | Glutaraldehyde treatment | Adsorption with no treatment |
| 0 | 10 | 10 | 13 | 6 |
| 1/6 | 80 | 24 | 145 | 66 |
| 0.5 | 83 | 27 | 160 | 84 |
| 6 | 89 | 42 | 155 | 85 |
| 30 | 74 | 51 | 149 | 97 |

TABLE 2

| Reflux time (hours) | Amino acid attachment capacity | | |
|---|---|---|---|
| | Amino acid attachment capacity μM/g | | |
| | Glu | Thr | 7-ADCA |
| 0 | 0 | 0 | 0 |
| 0.5 | 86 | 51 | 46 |
| 6 | 73 | 120 | 44 |
| 30 | 92 | 84 | 45 |

TABLE 3

| Amount of hydrochloric acid consumed by titration | |
|---|---|
| Reflux time | Content of amino groups μM/g |
| 5 min. | 175 |
| 1 hour | 263 |
| 5 hours | 300 |
| 8 hours | 275 |

Amount of the enzyme (penicillinacylase) adsorbed

In place of determining the amount of penicillinacylase produced from *Bacillus megaterium* B-400(FERM-P748) attached on the carrier in the preceding item (1), the activity of penicillinacylase is determined according to the penicillinacylase activity assay as previously described. The results are shown in Table 4.

TABLE 4

| Reflux time (hours) | Specific activity of penicillinacylase | |
|---|---|---|
| | Glutaraldehyde treatment U/mg | Adsorption with no treatment U/mg |
| 0 | 0.12 | 0.10 |
| 1/6 | 2.88 | 3.05 |
| 0.5 | 2.90 | 3.00 |
| 1 | 2.85 | 3.05 |
| 6 | 2.83 | 3.05 |

EXAMPLE 3

Into a three-necked flask is charged 2.5 g of lithium aluminum hydride and 100 ml of dry diethyl ether is added thereto, followed by stirring the mixture. To the resultant mixture is added 2 g of particles (average particle size: 100 mesh) of the porous acrylonitrile as prepared in Example 1 and the mixture is heated under reflux at 50° C. for 16 hours. After the reaction, to the reaction mixture is added dropwise water under ice-cooling to decompose unaltered lithium aluminum hydride. Further, by dropwise addition of 1 N hydrochloric acid, the decomposed product is dissolved. The aminated polyacrylonitrile is recovered by filtration and then washed successively with 1 N hydrochloric acid, water, 1 N sodium hydroxide, water and 0.1 M phosphate buffer (pH 7.5) to give pale yellow polyacrylonitrile particles containing amino groups having a porous structure (average particle diameter: 100 mesh).

EXAMPLE 4

A mixture of 2 g of lithium aluminum hydride with 50 ml of dry diethyl ether is stirred and to the mixture is added under cooling little by little 3 g of particles (average diameter: 100 mesh) of an acrylonitrile type copolymer having a porous structure comprising 55 parts of acrylonitrile, 25 parts of divinyl benzene and 20 parts of vinyl ethyl benzene prepared similarly as described in Example 1. The resultant mixture is heated under reflux at 45° C. for 10 minutes to 8 hours and then 2 ml of water is added to the reaction mixture with stirring under cooling in an ice-bath to decompose unaltered lithium aluminum hydride. Further, after addition of 1 N hydrochloric acid to the mixture, the insoluble polymer containing amino groups is separated by filtration and washed to give particles (average size: 100 mesh; wet weight=9 g) of an aminated polyacrylonitrile type copolymer having a porous structure.

The thus prepared aminated copolymer has the following physical and chemical properties:

Color: pale yellow, yellowish color being intensified as the reduction time is prolonged;

Viscosity: not measurable due to insolubility in the solvents as set forth below;

Solubility in solvents:: insoluble in DMSO, DMF, conc. nitric acid, 65% KSCN solution (60° C.), chloroform, acetonitrile, pyridine, nitromethane, cyclohexane, diethyl ether, and 30% aqueous sodium hydroxide solution;

Content of amino groups: estimated content of amino groups as measured by the hydrochloric acid titration method as described in Example 2 are as follows:

| Reduction time | Content of amino groups (amount of hydrochloric acid consumed) |
|---|---|
| 10 minutes | 545 μM/g-carrier |
| 1 hour | 738 |
| 8 hours | 780 |

The particles of the polyacrylonitrile copolymer having porous structure of the starting material (Control) and the particles of the aminated polyacrylonitrile copolymer having porous structure (present invention) have capacities for attaching various enzymes as prepared in the following Reference examples as set forth in the following Table:

| Enzyme | Present invention | Control |
|---|---|---|
| Acylase produced from *Bacillus megaterium* B-400 | 150 U/mg | 40 U/mg |
| Acylase produced from *Comamonas* sp. SY-77-1 | 670 U/mg | 350 U/mg |
| Cholineoxidase produced | | |

| Enzyme | Present invention | Control |
|---|---|---|
| from *Arthrobacter globiformis* B-0577 | 7.0 U/mg | 0.45 U/mg |

The above capacities are measured by the following method. Namely, 50 to 100 mg of the sample of the polymer according to the present invention or Control is added into an L-shaped test tube and a buffer containing each enzyme is added thereto. After stirring the mixture at 30° C. for 60 minutes, the reaction mixture is separated by filtration and washed with 0.5 N sodium chloride/0.1 M phosphate buffer (pH 7.5), followed by washing with 0.1 M phosphate buffer (pH 7.5). The product obtained is then subjected to the activity assay as described above.

REFERENCE EXAMPLE 1

Acylase produced from *Bacillus megaterium* B-400

Into an Erlenmeyer's flask of 500 ml capacity is apportioned 100 ml of a medium (pH 7.0) containing 1% polypeptone, 1% meat extract and 0.5% sodium chloride. After sterilization at 120° C. for 20 minutes, *Bacillus megaterium* B-400(FERM-P No. 748) is inoculated to the medium and shaking cultivation is conducted at 30° C. for 48 hours. After cultivation, the filtrate obtained by removing the microorganism cells is adjusted to pH 7.5 and 1 g of Celite (product of Johns Manville Sales Co. No. 560) is added thereto. The mixture is stirred for about 30 minutes and thereafter the Celite is separated by filtration. The resultant Celite is found to have an activity of 20.4 U/g. The thus prepared Celite (800 g) is suspended in water and packed in a column (size: 9.5×80 cm) and eluted with 24% ammonium sulfate/0.1 M tris-hydroxyaminomethane solution (pH 8.5) under the condition of space velocity of 0.5, whereby 210 ml (30 U/ml) of fractions having absorption at 280 nm are obtained. Then, the eluate, 120 ml, is charged into a column (size: 3.2×41 cm) packed with Biogel-P-10 (50 to 100 mesh) and equilibrated with 0.1 M phosphate buffer (pH 7.5) to effect gel filtration, whereby 120 ml of fractions having absorption at 280 nm containing no sodium chloride is obtained (21.6 U/ml). This solution is further packed in a dialysis tube and concentrated in one liter of 30% carbowax (average molecular weight: about 20,000)/0.1 M phosphate buffer (pH 7.5) to 24 ml, followed further by dialysis in 0.1 M phosphate buffer (pH 7.5) overnight to give 23 ml of concentrated acylase solution produced from *Bacillus megaterium* B-400 (120 U/ml).

REFERENCE EXAMPLE 2

Acylase produced from Comamonas sp. SY-77-1

Into a 5-liter Erlenmeyer's flask is charged 500 ml of a medium (pH 7.0) containing 1% peptone, 0.5% meat extract and 0.3% sodium chloride. After sterlization at 120° C. for 15 minutes, Comamonas SY-77-1 (FERM-P No. 2410) is inoculated to the medium. Cultivation is carried out under shaking at 30° C. for 24 hours and the resultant seed culture is added to 10 liter of a medium (pH 9.0) in a 20-liter jar fermenter containing 2% casein, 0.05% yeast extract, 0.4% corn steep liquor, 0.5% sodium glutamate, and 0.1% glutaric acid which has been sterilized at 130° C. for 30 minutes. After cultivation at 30° C. for 3 days under the conditions of aeration of 100%/min. and stirring of 300 r.p.m., the cultured product is separated under cooling by centrifuge to collect the microorganism cells to give about 100 g of wet microorganism cells. The cells are suspended in 500 ml of 0.1 M phosphate buffer (pH 7.0) and 25 ml of a surfactant Cation FB (trade mark: produced by Nippon Oil and Fats Co., Ltd., Japan) is added thereto. The mixture is stirred at room temperature for one hour and the microorganism cell residue is removed by centrifuge to obtain about 500 ml of supernatant. Four batches of supernatant prepared similarly are combined to give about 2000 ml of the supernatant (50,000 U/ml). Then, to 1170 ml of the solution obtained is added 90 g of Amberlite XAD-7 (produced by Rohm & Haas Co., U.S.A.) and the mixture is stirred at room temperature for 30 minutes, followed by filtration. The filtrate obtained (1150 ml: 46,600 U/ml) is charged into a column (size 3.4×26 cm) and 30 g of polyacrylonitrile filament having a porous structure is packed therein without incorporation of air bubbles. Then, the liquid in said column is permitted to flow out. After washing, the column is eluted (150 ml/hour) with 0.1 M phosphate buffer (pH 7.0) to give 124 ml of active fractions (140,800 U/ml).

REFERENCE EXAMPLE 3

Cholineoxidase produced from *Arthrobacter globiformis* B-0577

Into an Erlenmeyer's flask of 500 ml capacity is apportioned 100 ml of a medium (pH 7.2) containing 1.0% choline, 0.5% KCl, 0.1% $K_2HPO_2$, 0.05% $MgSO_4.7H_2O$, 0.25% yeast extract, 1.0% fish·soluble and 0.1% Desfoam CA 220. After sterilization at 120° C. for 20 minutes, *Arthrobacter globiformis* B-0577 (FERM-P No. 3518) is inoculated to the medium and cultivation is carried out at 30° C. for 24 hours. This seed culture is transplanted into a jar fermenter of 30-liter capacity containing 10 liters of a sterilized culture medium having the same composition as mentioned above, and cultivation is carried out at 30° C. for 2 days with stirring at 200 r.p.m. under aeration of sterilized air of 20 liter/min. The culture broth obtained is subjected to centrifuge to collect the microorganism cells. After washing the cells with one liter of a solution comprising 0.01 M tris-hydrochloride buffer (pH 8.0), 2 mM EDTA and 1% KCl, the cells are suspended in one liter of a solution comprising 0.01 M phosphate buffer, 2 mM EDTA and 1% KCl, followed by addition of 200 mg of lysozyme (lysozyme chloride, produced by Nagase Sangyo Co., Ltd., Japan), and the mixture is stirred at 37° C. for 30 minutes. Then, the mixture is subjected to centrifuge at 5,000 r.p.m. for 15 minutes and the resultant supernatant (total activity: 998 U, total protein weight: 7680 mg, specific activity: 0.13 U/mg) is mixed with one liter of acetone. After removal of the precipitated impurities, the mixture is further diluted with acetone to acetone concentration of 65%. The diluted mixture is subjected to centrifuge at 5,000 r.p.m. for 15 minutes and the resultant precipitates are recovered. The precipitates (total activity: 900 U; total protein weight: 580 mg; specific activity: 1.55 U/mg) are dissolved in 40 ml of a solution comprising 0.01 M tris-hydrochloride buffer (pH 8.0), 2 mM EDTA and 1% KCl. The insolubles are separated by centrifuge and 60 ml of an aqueous saturated ammonia sulfate solution is added thereto. After stirring the mixture for 15 minutes, the resultant mixture is subjected to centrifuge at 12,000 r.p.m. for 15 minutes to give precipitates (total activity: 825 U; total protein weight: 300 mg; specific activity: 2.75 U/mg). Then, the precipitates are dissolved in 15 ml of a solution comprising 0.01 M phosphate buffer (pH 7.0) and 2 mM EDTA. The resultant solution is charged at flow velocity of 30 ml/hour into a column packed with Sephadex G-25 (product of Pharmacia Co., Sweden) to effect desalting and the purified solution obtained is charged into a DEAE-cellulose column (size 2.0×7.0 cm) buffered at pH 7.0 to be adsorbed thereon. Subsequently, elution is effected by using ionic strength gradient of KCl from 0.2 M to 0.5 M and the eluted fractions at about 0.4 M KCl concentration are recovered to obtain 172 ml of active fractions (conditions: flow velocity=1.4 ml/min.; volume of one fraction=6 ml). These active fractions are further subjected to dialysis through a dialysis membrane of cellulose acetate using a solution comprising 5 mM phosphate buffer and 2 mM EDTA for 7 hours. The resultant dialysate is lyophilized and the product is further dissolved in 10 ml of a solution comprising 0.01 M tris-hydrochloride buffer (pH 8.0), 2 mM EDTA and 1% KCl. The resultant solution is subjected to chromatography by use of a column (size: 2.8×9.5 cm) packed with Sephadex G-200 under the conditions of flow velocity of 0.18 ml/min. and volume of one fraction of 6 ml. The fraction Nos. 42 to 48 are recovered and subjected to lyophilization, followed further by the same chromatographic operation as described above, to give cholineoxidase (total activity 380 U, total protein weight: 55.9 mg; specific activity: 6.80 U/mg).

REFERENCE EXAMPLE 4

Phospholipase D produced from *Streptomyces chromofuscus* A-0848

A medium (100 ml) containing 2% peptone, 2% lactose, 0.1% sodium chloride, 0.05% $K_2HPO_4$, 0.05% $MgSO_4.7H_2O$ and 0.5% Desfoam BC-51Y is apportioned into an Erlenmeyer's flask of 500 ml capacity and after sterilization at 120° C. for 20 minutes *Streptomyces chromofuscus* A-0848 (FERM-P 3519) is inoculated to said medium. Cultivation is carried out at 26° C. for 3 days and the resultant seed culture is transplanted in a 30-liter jar fermenter containing 20 liters of the medium having the same composition as mentioned above and cultivation is carried out at 26° C. for 2 days with stirring at 300 r.p.m. under aeration of 20 liter/min. to obtain a culture broth (0.5 U/ml). This culture broth is subjected to centrifuge to obtain about 18 liters of filtrate. Then, the filtrate is concentrated to about 3 liters, mixed with 2.4 liters of acetone, and the precipitates formed are removed by centrifugation. The supernatant is further mixed with 2 liters of acetone and the precipitates formed are recovered. The insolubles are removed by adding 500 ml of water to the precipitates. The precipitates after further addition of 330 ml of acetone to the mixture are recovered and dissolved in 200 ml of water. This solution is mixed with 200 ml of an aqueous saturated ammonium sulfate solution. The precipitates formed are recovered and dissolved in 50 ml of water and subjected to desalting by using Sephadex G-25, followed by lyophilization, to give 700 mg of phospholipase D powders (5 U/mg).

EXAMPLE 5

After washing 9 g of particles of the aminated polyacrylonitrile copolymer having a porous structure as prepared in Example 4 with 0.1 M phosphate buffer (pH 7.5), the washed particles are added into 200 ml of a previously cooled 12.5% glutaraldehyde/phosphate buffer (pH 8.5), followed by stirring at 0° C. for 20 minutes. This carrier is collected by filtration, sufficiently washed with 0.1 M phosphate buffer (pH 7.5) and added into 60 ml of a solution of the acylase enzyme (60 U/ml) produced from *Bacillus megaterium* B-400. After stirring the mixture at 4° C. overnight, the carrier is separated by filtration and washed with 0.5 M sodium chloride/0.1 M phosphate buffer (pH 7.5), and then with 0.1 M phosphate buffer (pH 7.5), to give 8.7 g immobilized material having bound said particles with the acylase (acylase activity: 324 U/g).

EXAMPLE 6

The immobilized material obtained in Example 5 having bound the glutaraldehyde-treated carrier with acylase is packed in a jacketed column (size: 1.2×8 cm). Into the column is charged at 37° C. 1% solution of 7-phenylacetamido-desacetoxy cephalosporanic acid in 0.1 M phosphate buffer (pH 7.5) at space velocity of 0.5 continuously for 20 days. The content of 7-ADCA in the resultant reaction mixture is measured by PDAB method, wherein absorption is measured at 415 nm after the reaction for 10 minutes using a buffer comprising 1 ml of 0.05 N NaOH and 2 ml of 2.0% acetic acid, and 0.5 ml of 0.5% p-dimethylaminobenzaldehyde methanol solution. From the measured value, the content is determined from the calibration curve of ADCA as shown in FIG. 2, wherein the volume of the reactant/column volume and days for charging are indicated on abscissa versus the yield of 7-ADCA on ordinate. As apparently seen from the result shown in FIG. 2, the immobilized enzyme of the present invention can be used for a very long time.

EXAMPLE 7

A mixture of 3.8 g of lithium aluminum hydride with 120 ml of dry diethyl ether is added to 2.5 g of polyacrylonitrile fibers (acrylonitrile 95%; thickness 20 to 35 microns). The reduction reaction is carried out at 45° C. for 24 hours under stirring. Then, with stirring under cooling in an ice-bath, 3 ml of water is added dropwise to the reaction mixture. Further, 1 N HCl is added little by little to the mixture until generation of hydrogen gas is stopped, whereupon the product is separated by filtration to give 12.5 g (wet weight) of aminated polyacrylonitrile fibers having a porous structure.

As the next step, 600 mg (wet weight) of the fibers as prepared above are washed with 0.1 M phosphate buffer (pH 7.5) and added into 50 ml of a cooled 12.5% glutaraldehyde/phosphate buffer (pH 8.5), followed by stirring at 0° C. for 20 minutes. The treated fibers are separated by filtration and then washed with 0.1 M phosphate buffer (pH 7.5). The resultant carrier is added into 8 ml of an acylase solution (108,000 U/ml) produced from Comamonas sp. SY-77-1 and the mixture is stirred at room temperature for 5 minutes. After addition of 10 μl of 25% glutaraldehyde, the mixture is further stirred at 30° C. for 60 minutes. Then, the product is separated by filtration to recover solid components, which are washed with 0.5 M sodium chloride/0.1 M phosphate buffer (pH 7.5) and then with 0.1 M phosphate buffer (pH 7.5) to obtain 300 mg (wet weight) of immobilized enzyme having bound acylase to the said fibrous carrier (acylase activity 1600 U/mg).

Subsequently, 4.5 g (wet weight) of the thus prepared immobilized enzyme is packed in a jacketed column (1×5 cm, V=4 ml) and washed with 0.1 M phosphate buffer (pH 7.5). Into the column is continuously charged at space velocity of 1.5 a solution of 9.92 mg/ml of 7-(4-carboxybutaneamido)-cephalosporanic acid in 0.1 M phosphate buffer. The effluent containing 7-amino-cephalosporanic acid (7-ACA) is subjected to measurement by PDAB method and its content is determined from the calibration curve of 7-ACA. FIG. 3 shows the calibration curve of 7-ACA with the amount of the liquor passed on abscissa versus percentage of cleavage which is the yield of 7-ACA on ordinate. It can clearly be seen that the immobilized enzyme of the present invention can be used favorably for a long time without deterioration in enzyme activity. Furthermore, 600 ml of the effluent containing 7-ACA as mentioned above (percentage of cleavage=84.5%) is adjusted to pH 3.2, concentrated to about 55 ml and left to stand at 4° C. overnight, whereby 3.22 g of 7-ACA precipitates (purity=86.3%) are obtained.

EXAMPLE 8

The aminated acrylonitrile fibers as prepared in Example 7 (0.6 g, wet weight) are added into 50 ml of an ice-cooled 12.5% glutaraldehyde/borate buffer (pH 8.5) and the mixture is stirred at 0° C. for 20 minutes. Then, said fibers are separated by filtration and washed with borate buffer (pH 8.5) and then with 0.1 M phosphate buffer (pH 7.5). The treated fibers are mixed with 12 ml of a 0.1 M phosphate buffer solution (pH 7.5) containing 20 U/ml of phospholipase D and 5 U/ml of cholineoxidase, and the mixture is stirred at 0° C. overnight. The product is separated by filtration and washed with 0.5 M sodium chloride/0.1 M phosphate buffer (pH 7.5) to give immobilized enzyme having phospholipase D and cholineoxidase bound to said fibrous carrier (phospholipase D activity: 119 U/g, cholineoxidase activity: 17 U/g).

The immobilized enzyme obtained is provided for use in combination with the device comprising the parts 1 to 7 as shown in FIG. 1(b). Namely, said immobilized enzyme is packed in the column 1 (size: 5×3.5 cm). From the sample inlet B is flown a substrate solution comprising 0.01 M tris-aminomethane hydrochloride buffer containing 0.3% Triton X-100 and 0.01 M CaCl$_2$ at flow velocity of 20 ml/hour to bring the system into a steady state. Then, from the sample inlet B' are injected phospholipid solutions of various concentrations of 5 μl. By injection of the phospholipid solution, the phospholipid is subjected in the column 1 containing the immobilized enzyme to enzymatic decomposition by phospholipase D and cholineoxidase, whereby the dissolved oxygen is consumed in the choline oxidation by cholineoxidase. This consumption is measured by the measuring part 2 (flow cell) having the oxygen electrode 3 and recorded by dissolved oxygen meter 5 on the recorder 6. FIG. 4 shows the calibration curve from the phospholipid concentrations and the peak areas recorded according to such a method. Based on this calibration curve, it is possible to conduct quantitative determination of a phospholipid contained in blood by injection of a serum component through the sample inlet B. Typical example of this reaction is illustrated with reference to lecithin, which undergoes reaction according to the following reaction scheme. The consumption of oxygen represented by O$_2$ in the reaction scheme is to be measured.

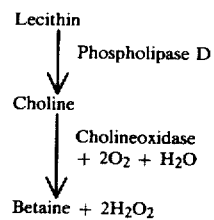

Furthermore, using lecithin as substrate in solutions of 1 mM, 2 mM and 3 mM concentrations and injecting each 10 μl of the solutions, the change in peak area value depending on the number of repeated uses is determined under the condition of flow velocity of 38 ml/hour and chart speed of 300 mm/hour to give the result as shown in FIG. 5.

As described above, remarkably accurate values can be given by the measurement by use of this immobilized enzyme, as clearly seen from FIG. 4. In addition, FIG. 5 shows substantially stable performance at various concentrations.

EXAMPLE 9

The polyacrylonitrile as obtained in Example 1 is similarly dissolved in dimethylformamide and a membrane is formed from the resultant solution in a water-bath containing 15% dimethylformamide. The membrane is washed with water and dried on air to give an polyacrylonitrile membrane. This membrane (450 mg) is heated under reflux in the presence of 700 mg of lithium aluminum hydride and 30 ml of diethyl ether for 18 hours to give 520 mg (wet weight) of an aminated polyacrylonitrile membrane having a porous structure. Then, 150 mg of this membrane is mixed with 40 ml of 12.5% glutaraldehyde/borate buffer (pH 8.5) and the mixture is stirred at 0° C. for 20 minutes. The treated membrane is separated by filtration and mixed with stirring at 30° C. for 60 minutes with 5 ml of a 0.1 M phosphate buffer (pH 7.5) containing 15 mg of cholineoxidase (3.6 U/mg). The product is separated by filtration and washed with 0.5 M sodium chloride/0.1 M phosphate buffer (pH 7.5), and then with 0.1 M phosphate buffer (pH 7.5), to give an immobilized enzyme having cholineoxidase bound to said membrane (cholineoxidase activity 3 U/g).

Then, this immobilized enzyme is cut into a strip of 5 mm×5 mm. Using the device as shown in FIG. 1(c), this strip is attached to the oxygen electrode 3, covered with a nylon net and equipped at the measuring part 2. The whole assembly is set in the thermostat bath 7. Subsequently, into the measuring part 2 is injected from the inlet B one ml of 0.01 M tris buffer (pH 8.0) to stabilize the dissolved oxygen value, followed by injection of choline chloride solutions of various concentrations of each 20 μl. The results are recovered on the recorder 6 connected to the meter 5 (dissolved oxygen meter) equipped with a differential converter. From the concentrations of the choline chloride and corresponding maximum velocity differentials (dtO$_2$), the calibration curve is determined as shown in FIG. 6. FIG. 7 also shows the difference in values depending on the number of repeated uses by using 20 μl of 0.016 M choline chloride. From these results, the immobilized enzyme can give accurate measurement values which are also very stable.

EXAMPLE 10

The same aminated polyacrylonitrile membrane as used in Example 9 (10 mg; wet weight) is mixed with stirring at 0° C. for 20 minutes with 40 ml of a 12.5% glutaraldehyde/borate buffer (pH 8.5). After filtration and washing with 0.1 M phosphate buffer (pH 7.5), the treated membrane is mixed with stirring at 30° C. for 60 minutes with 5 ml of 0.1 M phosphate buffer (pH 7.5) containing 10 mg of glucoseoxidase (produced by Behlinger Co.) (210 U/mg). Then, the product is separated by filtration and washed with 0.5 M sodium chloride/0.1 M phosphate buffer (pH 7.5) and further with 0.1 M phosphate buffer (pH 7.5) to give an immobilized enzyme (glucoseoxidase activity 150 U/g) having glucoseoxidase bound to said membrane.

The above immobilized enzyme is cut into a strip of 5 mm×5 mm and provided for use in the device as described in Example 9. The same measurement is performed as in Example 9 except that glucose is used in place of choline chloride.

As the result, there are obtained the calibration curve as shown in FIG. 8 and the stability after repeated uses as shown in FIG. 9, indicating excellent accurate and stable measurement values.

EXAMPLE 11

A solution of 160 mg (3.6 U/mg) of cholineoxidase dissolved in 5 ml of 0.1 M phosphate buffer (pH 7.5) is mixed with stirring in an ice-bath with 100 mg (wet weight) of the aminated polyacrylonitrile fibers as obtained in Example 7. To this mixture is added 20 μl of 1-ethyl-3-(3-dimethylaminopropyl)carbodiimide and the mixture is adjusted with 1 N HCl to pH 7.5. The mixture is stirred in an ice-bath for 3 hours and further at 4° C. overnight. The product is separated by filtration and washed with 0.5 M sodium chloride/0.1 M phosphate buffer (pH 7.5) and then with 0.1 M phosphate buffer (pH 7.5) to give immobilized enzyme having cholineoxidase bound to said fibrous carrier (cholineoxidase activity: 5.6 U/mg).

EXAMPLE 12

Example 11 is repeated except that 5 ml of acylase solution (96 U/ml) produced from *Bacillus megaterium* B-400 in place of cholineoxidase and 40 μl of 1-ethyl-3-(3-dimethylaminopropyl)carbodiimide are used, whereby there is obtained an immobilized enzyme having acylase bound to said fibrous carrier (acylase activity: 264 U/g).

EXAMPLE 13

The particles of the aminated polyacrylonitrile copolymer as obtained in Example 4 (500 mg; wet weight) are mixed with stirring at 0° C. for 20 minutes with 30 ml of 12.5% glutaraldehyde/borate buffer (pH 8.5). The treated particles are separated by filtration and thoroughly washed with 0.1 M phosphate buffer (pH 7.5). The particles are then mixed with stirring at 4° C. for 24 hours with 30 ml of 0.5 M aqueous hexamethylene diamine solution (pH 9.5), followed by filtration and thorough washing with water. Further, the product is treated with 12.5% glutaraldehyde/borate buffer (pH 8.5), followed by washing with water, and mixed with stirring at 4° C. for 12 hours with 5 ml of an acylase solution (72 U/ml) produced from *Bacillus megaterium* B-400 (FERM-P 748). After filtration and washing with 0.5 M sodium chloride/0.1 M phosphate buffer (pH 7.5), and then with 0.1 M phosphate buffer (pH 7.5), there is obtained 440 mg (wet weight) of an immobilized enzyme having acylase bound to said particulate carrier (acylase activity: 250 U/g).

EXAMPLE 14

In a jar fermenter of 30-liter capacity are charged 20 liters of a medium (pH 6.0) comprising 2% glucose, 0.4% potassium hydrogen phosphate, 0.1% magnesium sulfate, 0.05% potassium chloride, 0.0025% ferrous sulfate, 0.1% yeast extract and 0.3% DL-methionine. After sterilization at 120° C. for 20 minutes, *Trigonopsis variabilis* CBS 4095 is inoculated to the medium and cultivation is carried out at 30° C. for 48 hours to obtain about 20 liters of culture broth. The culture broth is subjected to filtration to obtain about 400 g of microorganism cells. The microorganism cells are then dispersed in 800 ml of 0.1 M phosphate buffer (pH 7.5) and sufficiently crushed with addition of 1000 g of glass beads (diameter: 0.25 to 0.30 mm). The mixture is subjected to centrifugation under cooling at 15,000 r.p.m. for 20 minutes and the resultant supernatant (D-amino acid oxidase activity 15,000 U/ml), 1000 ml, is treated with Carbowax (average molecular weight=about 20,000) to obtain 100 ml of concentrated solution of D-amino acid oxidase (145,000 U/ml).

To the thus prepared concentrated solution (10 ml) in an L-shaped test tube is added one gram of the polyacrylonitrile (acrylonitrile: 95%) fiber having a porous structure (as Control) or the aminated polyacrylonitrile (acrylonitrile: 95%) fiber as prepared in Example 7 (as Present invention). Each mixture is stirred at 30° C. for 60 minutes. The product is separated by filtration and washed with water. The enzyme attached on each fibrous carrier is assayed for its activity to give the result of D-amino acid oxidase activity for the fibrous carrier of Controls of 7.5 U/mg (attachment percentage: 0.5%) and that for the fibrous material of the present invention of 276 U/mg (attachment percentage: 19.0%), the latter being by far superior to the former.

The activity of said D-amino acid oxidase is conducted by the following method. That is, a system comprising 0.5 ml of the enzyme solution and 1.0 ml of 0.1 M phosphate buffer (pH 7.5) (or immobilized enzyme of the present invention and 1.5 ml of 0.1 M phosphate buffer of pH 7.5), 0.5 ml of an indicator (prepared by dissolving 5 mg O-dianisidine in one ml of ethanol, adding 0.3 ml of the resultant solution to 10 ml of 0.1 M phosphate buffer and further adding 2 mg of peroxidase 8 U/mg thereto) and 0.5 ml of 2% aqueous alanine solution is allowed to react at 37° C. for 15 minutes. The reaction is terminated by adding 0.5 ml of 50% Trichloro acetic acid to the reaction mixture and 2.0 ml of ethanol is further added thereto, followed by centrifugation at 10,000 r.p.m. for 5 minutes. The supernatant is recovered and subjected to measurement of absorption at 400 nm. The enzyme activity which changes the absorption by 0.100 after the reaction time of 15 minutes is determined as 100 U.

EXAMPLE 15

A mixture of 1.5 g of polyacrylonitrile fibers (acrylonitrile: 90% or more) having a porous structure with 120 ml of dry diethyl ether containing 1.5 g of lithium aluminum hydride is heated under reflux in an oil-bath at 50° C. for 21 hours. Then, the reduced product is separated by filtration and washed successively with ether, a small amount of water, 1 N HCl, water, 1 N NaOH, water and 0.1 M phosphate buffer (pH 7.5) to prepare an aminated polyacrylonitrile fiber (7 g as wet weight) having a porous structure.

Then, the fibers are added into 240 ml of a cooled 12.5% glutaraldehyde/borate buffer (pH 8.5) and the mixture is stirred at 0° C. for 20 minutes. The treated fibers are separated by filtration, washed with borate buffer (pH 8.5) and then with 0.1 M phosphate buffer (pH 7.5). The resultant fibers and 113 ml of an acylase solution (60 U/ml) produced from *Bacillus megaterium* B-400 (FERM-P 748) are mixed with stirring at room temperature for 4 hours and left to stand at 5° C. overnight. The product is separated by filtration (no acylase activity being recognized in the filtrate). The product is further washed with 0.5 M sodium chloride/0.1 M phosphate buffer (pH 7.5) and 0.1 M phosphate buffer (pH 7.5) to give 6.8 g (wet weight) of immobilized enzyme having the acylase bound to said fibrous carrier (584 U/g).

Subsequently, the immobilized enzyme is provided for use in the production device as shown in FIG. 10. That is, in FIG. 10, the above immobilized enzyme is packed in the jacketed column 9 (size: 1.6×6 cm). While maintaining the column at 37° C., the cooling tank 12 of 500 ml capacity is provided on the magnetic stirrer 10 in order to cool the storage tank 11 of 50 ml capacity in an ice-bath. In the cooled storage tank 11 is charged 50 ml of a solution of 4.455 g potassium benzylpenicillanate in 0.02 M phosphate buffer (pH 7.5) which is adjusted to pH 8.0 with 1 N NaOH. The solution is passed through the jacket 13 maintained at 37° C. for heat exchange into the column 9 at the flow velocity of 21 ml/min. The solution passed through the column 9 is circulated by the pump 14 to the storage tank 11. The storage tank 11 is further equipped with the pH meter 15 in order to adjust the change in pH caused by the solution passed through the column 9 using 4 N NaOH at pH 7.8 to 8.2. Circulation of this solution is continued for 3 hours and thereafter the solution in the storage tank 11 and about 10 ml of washing liquid through the column 9 are recovered and combined. To the combined solution is added 30 ml of acetone and the mixture is adjusted to pH 4.2 with 6 N HCl. After the mixture is left to stand at 5° C. overnight, the precipitates formed are collected, washed with acetone and dried to give 2.16 g (purity: 96%) of 6-amino penicillanic acid.

When the above procedure is repeated ten times, there is no decrease in yield of 6-aminopenicillanic acid.

EXAMPLE 16

Particles (2 g of an acrylonitrile type copolymer; about 100μ in diameter) comprising 55 parts of acrylonitrile, 25 parts of divinyl benzene and 20 parts of vinyl ethyl benzene having a porous structure are subjected to nitration in 47% nitric acid sulfuric acid mixture at 0° C. for 60 minutes. After washing with water, the product is reduced in a 6% sodium hydrosulfite/2 N aqueous KOH solution at 60° C. for 2 hours. The resultant product is thoroughly washed with water to give 5.5 g (wet weight) of aminated polyacrylonitrile type copolymer having a porous structure.

The thus prepared particles (90 mg as wet weight) are stirred in a 12.5% glutaraldehyde/borate buffer (pH 8.5) at 0° C. for 20 minutes, followed by washing with 0.1 M phosphate buffer (pH 7.5). Then, the treated particles are mixed with 3 ml of an acylase solution (84 U/ml) produced from *Bacillus megaterium* B-400 (FERM-P 748) with stirring at 30° C. for 60 minutes. The product is collected by filtration and washed with 0.05 M sodium chloride/0.1 M phosphate buffer (pH 7.5) and with 0.1 M phosphate buffer (pH 7.5) to prepare an immobilized enzyme (118 U/g) having the acylase bound to said particulate carrier. This product can be used in the various devices as explained in the foregoing Examples.

EXAMPLES 17 TO 19

(a) A three-necked flask of 500 ml capacity is equipped with a pipe for introducing nitrogen, a stirrer and a reflux condenser. The flask is dipped in a thermostat water-bath maintained at about 40° C. and replaced with nitrogen for 15 minutes. Then, into this flask is charged 120 ml of distilled water having 1 g of sodium alkyl sulfonate dissolved therein. While stirring the solution, 70 g of acrylonitrile and 10 g of styrene free from inhibitors are added thereto to be emulsified, followed by addition of 0.1 g of potassium persulfate. The polymerization is conducted for 20 to 22 hours to prepare emulsions containing particles of 0.1 to 1.0μ in diameter. The resultant emulsion is poured into 500 ml of water and coagulated with sodium chloride under stirring. The product of acrylonitrile-styrene copolymer is filtered, washed with water and dried, followed by removal of unaltered monomers under reduced pressure. The copolymer has an intrisic viscosity of 1.3 in dimethylformamide. This copolymer (10 g) is dissolved in 200 ml of dimethylformamide and the solution is added dropwise by an atomizer cup into 50 liters of a 20% aqueous acetone solution to prepare hydrated particles having a porous structure (size: 0.5 to 1 mm).

(b) Using the same apparatus as described in (a), a mixture of 300 ml of distilled water containing 2 g of Triton 720 (produced by Rohm & Haas Co., U.S.A.) and 2 g of Tergitol (produced by Union Carbide Co., U.S.A.) therein with 0.2 g of potassium persulfate is stirred and 80 g of acrylonitrile, from which inhibitors are previously removed, and 20 g of distilled methyl acrylate are added thereto. Polymerization is conducted by heating at 40° to 50° C. After 30 minutes, polymerization is carried out at reflux temperature of 90° C. After the reaction, the resultant suspension is subjected to steam distillation for 15 to 20 minutes to remove unaltered monomers. Then, after the product is salted out similarly as in (a) and dried on air, there is obtained an acrylonitrilemethyl acrylate copolymer having an intrinsic viscosity of 1.2 in dimethylformamide. This copolymer (10 g) is dissolved in 100 ml of dimethylsulfoxide and the solution is added dropwise by an atomizer cup into a 20% aqueous dimethylsulfoxide solution to prepare particles (0.5 to 1 mm in diameter) of said copolymer in the form of hydrated gels having a porous structure.

(c) The procedure as described in (a) is repeated except that 10 g of divinyl benzene is used in place of styrene to prepare particles (0.5 to 1 mm in diameter) of acrylonitrile-divinyl benzene copolymer in the form of hydrated gels having a porous structure.

Using each 2 g of the particles of the copolymers having porous structure as obtained in the above (a), (b) and (c), the following reduction reaction is carried out. Namely, 2.5 g of lithium aluminum hydride is added into a three-necked flask and stirred with 100 ml of dry diethyl ether. To the mixture is added 2 g of each copolymer and the reaction is conducted under heating with reflux at constant temperature at 50° C. for 16 hours. After the reaction, the product is treated with water and 1 N HCl in an ice-bath, followed by successive washing with 1 N HCl, water, 1 N NaOH, water and 0.1 M phosphate buffer (pH 7.5), to prepared particles having a porous structure containing free amino groups and nitrile groups.

Each of the above particles having porous structure containing free amino groups and nitrile groups (300 mg as wet weight) is treated with 50 ml of an ice-cooled 12.5% glutaraldehyde/borate buffer (pH 8.5) with stirring at 0° C. for 20 minutes. The treated fibers are collected by filtration and washed with 0.1 M phosphate buffer (pH 7.5). Then, the particles are added into 3 ml of an acylase solution (72 U/ml) produced from *Bacillus megaterium* B-400 (FERM-P 478) in an L-shaped test tube and the mixture is stirred at 30° C. for 60 minutes. The product is filtered, washed with 0.5 M sodium chloride/0.1 M phosphate buffer (pH 7.5) and then with 0.1 M phosphate buffer (pH 7.5) to give objective immobilized enzymes having acylase bound to the particulate carriers, respectively.

Furthermore, using the particles of the aminated polyacrylonitrile having a porous structure prepared in Example 3, acylase is found similarly as described above thereto to prepare an immobilized enzyme.

As the result, the acylase activity in the immobilized enzyme using the copolymer as obtained in (a) is found to be 162 U/g; that in (b) 216 U/g; that in (c) 192 U/g; and that, using the aminated polyacrylonitrile obtained in Example 3, 252 U/g, respectively.

EXAMPLE 20

The particles of the aminated polyacrylonitrile having porous structure obtained in Example 3 (1.5 g) are dipped in 25 ml of acetone and one ml of triethylamine is added to the mixture. To the resultant mixture is further added dropwise 12 ml of a solution containing 1 g of succinic acid anhydride in acetone over 5 minutes and stirring is continued for 6 hours. After the reaction, the reaction product is separated by filtration, washed with water, then with 1 N HCl, followed by washing with water, and then dried. Then, 1 g of the reaction product is charged into an Erlenmeyer's flask of 50 ml capacity and mixed with 3 ml of dioxane and 1 g of N-hydroxysuccinimide. While stirring the mixture under ice-cooling, 2 ml of dioxane containing 1 g of N,N'-dicyclohexylcarbodiimide dissolved therein is added dropwise thereto over about 10 minutes, and the mixture is left to stand at 10° C. overnight. After the reaction, the product is separated by filtration and washed by decantation using 20 times as much as its volume of dioxane. After removal of the insolubles, the product is further washed with dioxane and dried under reduced pressure. The reaction product having active esters (30 mg) is sufficiently swelled in 0.1 M phosphate buffer (pH 7.5), followed by filtration, and added into 5 ml of an acylase solution (7.2 U/ml) produced from *Bacillus megaterium* B-400 (FERM-P 748). After the reaction is carried out while stirring the mixture at pH 7.5 for 4 hours in an ice-bath, the product is filtered and washed with 0.1 M phosphate buffer (pH 7.5). Then, in 1 M glycine/0.1 M phosphate buffer (pH 7.5), stirring is continued at room temperature for 60 minutes to eliminate unaltered active ester groups. After filtration, the solid phase is washed with 0.5 M sodium chloride/0.1 M phosphate buffer (pH 7.5), and further with 0.1 M phosphate buffer (pH 7.5), to give 840 mg (wet weight) of the immobilized enzyme having acylase bound to said particulate carrier (177.6 U/g).

What we claim is:

1. An immobilized material comprising a biologically active enzyme bound by covalent bonding with a crosslinking agent or condensing agent onto a carrier which is a water-insoluble acrylonitrile polymer containing from 20 μM to 1000 μM of amino groups per gram of the polymer and having a porous structure containing a number of micro-pores with an average size of from 40 to 9000 Å, said acrylonitrile polymer being produced by effecting reduction of an acrylonitrile polymer having said porous structure in an inert non-solvent with lithium aluminum hydride.

2. An immobilized material according to claim 1, wherein the acrylonitrile polymer containing amino groups is shaped in the form of a fiber, a particle, a membrane or a hollow filament.

3. An immobilized material according to claim 2, wherein the acrylonitrile polymer contains amino groups in an amount which does not make the polymer substantially soluble in water.

4. An immobilized material according to claim 1, wherein the acrylonitrile polymer is a polymer of an acrylonitrile monomer or a copolymer of said monomer with a comonomer containing ethylenically unsaturated double bond.

5. An immobilized material according to claim 4, wherein the acrylonitrile monomer is acrylonitrile, methacrylonitrile, α-chloroacrylonitrile or cinnamnitrile.

6. An immobilized material according to claim 4, wherein the comonomer is a styrene monomer, an acrylic acid ester monomer, a conjugated diene, a halogenated olefin, a vinyl ether monomer, a vinyl ketone monomer, a vinyl ester monomer, an amide vinyl monomer, a basic monomer or a polyfunctional monomer.

7. An immobilized material according to claim 4, wherein the acrylonitrile polymer comprises polyacrylonitrile containing 90% or more of acrylonitrile shaped in the form of a fiber, a particle, a membrane or a hollow filament.

8. An immobilized material according to claim 4, wherein the acrylonitrile polymer is a copolymer consisting of acrylonitrile, divinyl benzene and vinyl ethyl benzene shaped in the form of a fiber, a particle, a membrane or a hollow filament.

9. An immobilized material according to claim 1, wherein said covalent bonding is effected directly through said crosslinking agent or condensing agent or through said crosslinking agent or condensing agent and through an intermediary spacer.

10. An immobilized material according to claim 9, wherein said crosslinking agent is glutaraldehyde.

11. An immobilized material according to claim 9, wherein said crosslinking agent is glutaraldehyde, crotonaldehyde, acrolein, hexamethylenediamine diisocyanate, hexamethylene-iso-thiocyanate, toluene diisocyanate, xylene diisocyanate, dimethyl adipiimidate, dimethyl suberiimidate, dimethyl-3,3'-dithio-bis-propionimidate or succinic acid anhydride.

12. An immobilized material according to claim 9, wherein said condensing agent is 1-ethyl-3-(3-dimethylamino-propyl)-carbodiimide.

13. An immobilized material according to claim 9, wherein said spacer is an alkylene diamine.

14. A process for preparing an immobilized material which comprises binding a carrier of a water-insoluble acrylonitrile polymer containing from 20 μM to 1000 μM of amino groups per gram of the polymer with a biologically active enzyme by covalent bonding with a crosslinking agent or condensing agent in an inert medium; said polymer having a porous structure containing a number of micro-pores with an average size of 40 to 9000 Å, said acrylonitrile polymer being produced by effecting reduction of an acrylonitrile polymer having said porous structure in an inert non-solvent with lithium aluminum hydride.

15. A process according to claim 14, wherein the acrylonitrile polymer containing amino groups is shaped in the form of a fiber, a particle, a membrane or a hollow filament.

16. A process according to claim 14 or claim 15, wherein the acrylonitrile polymer contains amino groups in an amount which does not make the polymer substantially soluble in water.

17. A process according to claim 14, wherein the acrylonitrile polymer is a polymer of an acrylonitrile monomer or a copolymer of said monomer with a comonomer containing ethylenically unsaturated double bond.

18. A process according to claim 17, wherein the acrylonitrile monomer is acrylonitrile, methacrylonitrile, α-chloroacrylonitrile or cinnamnitrile.

19. A process according to claim 17, wherein the comoner is a styrene monomer, an acrylic acid ester monomer, a conjugated diene, a halogenated olefin, a vinyl ether monomer, a vinyl ketone monomer, a vinyl ester monomer, an amide vinyl monomer, a basic monomer or a polyfunctional monomer.

20. A process according to claim 17, wherein the acrylonitrile polymer comprises polyacrylonitrile containing 90% or more of acrylonitrile shaped in the form of a fiber, a particle, a membrane or a hollow filament.

21. A process according to claim 17, wherein the acrylonitrile polymer is a copolymer consisting of acrylonitrile, divinyl benzene and vinyl ethyl benzene shaped in the form of a fiber, a particle, a membrane or a hollow filament.

22. A process according to claim 14, wherein covalent bonding is effected directly through said crosslinking agent or condensing agent or through said crosslinking agent or condensing agent and through an intermediary spacer.

23. A process according to claim 22, wherein the crosslinking agent is glutaraldehyde, crotonaldehyde, acrolein, hexamethylenediamine diisocyanate, hexamethylene-iso-thiocyanate, toluene diisocyanate, xylene diisocyanate, dimethyl adipiimidate, dimethyl suberiimidate, dimethyl-3,3'-dithio-bis-propionimidate or succinic acid anhydride.

24. A process according to claim 22, wherein the condensing agent is 1-ethyl-3-(4-dimethylaminopropyl)-carbodiimide.

25. A process according to claim 22, wherein the spacer is an alkylene diamine.

26. A device for promoting an enzymatic reaction comprising a means containing an immobilized material having a biologically active enzyme bound by covalent bonding with a crosslinking agent or condensing agent to a carrier comprising a water-insoluble acrylonitrile polymer containing amino groups and having a porous structure having a number of micro-pores with an average pore size of 40–9000 Å, said polymer containing 20 µM to 1000 µM of amino groups per gram of the polymer and said acrylonitrile polymer being produced by effecting reduction of an acrylonitrile polymer having said porous structure in an inert nonsolvent with lithium aluminum hydride, a storage means containing a liquid substrate on which said biologically active enzyme has an activity and means for transporting at least a portion of the substrate from said storage means to said immobilized material.

27. A device according to claim 26, wherein the acrylonitrile type polymer is shaped in the form of a fiber, a particle, a membrane or a hollow filament.

28. A device according to claim 27, wherein the acrylonitrile type polymer contains amino groups in an amount which does not make the polymer substantially soluble in water.

29. A device according to claim 26, wherein the acrylonitrile polymer is a polymer of an acrylonitrile monomer or a copolymer of said monomer with a comonomer containing ethylenically unsaturated double bond.

30. A device according to claim 29, wherein the acrylonitrile monomer is acrylonitrile, methacrylonitrile, α-chloroacrylonitrile or cinnamnitrile.

31. A device according to claim 29, wherein the comonomer is a styrene monomer, an acrylic acid ester monomer, a conjugated diene, a halogenated olefin, a vinyl ether monomer, a vinyl ketone type monomer, a vinyl ester monomer, an amide vinyl monomer, a basic monomer or a polyfunctional monomer.

32. A device according to claim 29, wherein the acrylonitrile polymer comprises polyacrylonitrile containing 90% or more of acrylonitrile shaped in the form of a fiber, a particle, a membrane or a hollow filament.

33. A device according to claim 29, wherein the acrylonitrile polymer is a copolymer consisting of acrylonitrile, divinyl benzene and vinyl ethyl benzene shaped in the form of a fiber, a particle, a membrane or a hollow filament.

34. A device according to claim 26, wherein the enzymatic reaction system is a system for detecting electrical change caused by said enzymatic reaction.

35. A device according to claim 34, wherein the electrical change caused by the enzymatic reaction system is a change caused by the oxidizing ability of the reaction product.

36. A device according to claim 26, wherein said means containing the immobilized material comprises a packed column having an inlet and an outlet through which the liquid substrate can pass and the storage means for the liquid substrate comprises a cooled storage tank equipped with a stirrer for effecting agitation of the liquid substrate contained therein and said means for transporting the liquid substrate comprises a conduit means and operatively associated pump means for withdrawing liquid substrate from the storage means and passing the liquid substrate through the packed column and thereafter returning the treated liquid substrate to the said storage means.

37. A device according to claim 36, wherein the storage tank is equipped with a pH meter for adjusting a change in pH within the liquid substrate contained in said tank.

38. A device according to claim 36, wherein said conduit means further includes a heat exchanger for maintaining the liquid substrate at a temperature which will promote reaction with the enzyme bound to the carrier.

39. A device according to claim 26, wherein said covalent bonding is effected directly through said crosslinking agent or condensing agent or through said crosslinking agent or condensing agent and through an intermediary spacer.

40. A device according to claim 39, wherein said crosslinking agent is glutaraldehyde.

41. A device according to claim 39, wherein the crosslinking agent is glutaraldehyde, crotonaldehyde, acrolein, hexamethylenediamine diisocyanate, hexamethylene-iso-thiocyanate, toluene diisocyanate, xylene diisocyanate, dimethyl adipiimidate, dimethyl suberiimidate, dimethyl-3,3'-dithio-bix-propionimidate or succinic acid anhydride.

42. A device according to claim 39, wherein said condensing agent is 1-ethyl-3-(3-dimethylaminopropyl)-carbodiimide.

43. A device according to claim 39, wherein said spacer is an alkylene diamine.

44. A method for effecting an enzymatic reaction by use of an immobilized material, which comprises reacting an immobilized material comprising a biologically active enzyme bound to a carrier by covalent bonding, with a crosslinking agent or condensing agent, said carrier comprising an acrylonitrile polymer containing amino groups and having a porous structure having a number of micro-pores with an average pore size of 40–9000 Å, said polymer containing 20 μM to 1000 μM of amino groups per gram of the polymer and acrylonitrile polymer being produced by effecting reduction of an acrylonitrile polymer having said porous structure in an inert non-solvent with lithium aluminum hydride, with a substrate on which said biologically active enzyme has activity.

45. A method according to claim 44, wherein the acrylonitrile polymer containing amino groups is shaped in the form of a fiber, a particle, a membrane or a hollow filament.

46. A method according to claim 44 or claim 45, wherein the acrylonitrile type polymer contains amino groups in an amount which does not make the polymer substantially soluble in water.

47. A method according to claim 44, wherein the acrylonitrile type polymer is a polymer of an acrylonitrile monomer or a copolymer of said monomer with a comonomer containing ethylenically unsaturated double bond.

48. A method according to claim 47, wherein the acrylonitrile monomer is acrylonitrile, methacrylonitrile, α-chloroacrylonitrile or cinnamnitrile.

49. A method according to claim 47, wherein the comonomer is a styrene monomer, an acrylic acid ester monomer, a conjugated diene, a halogenated olefin, a vinyl ether monomer, a vinyl ketone monomer, a vinyl ester monomer, an amide vinyl monomer, a basic monomer or a polyfunctional monomer.

50. A method according to claim 47, wherein the acrylonitrile polymer comprises polyacrylonitrile containing 90% or more of acrylonitrile shaped in the form of a fiber, a particle, a membrane or a hollow filament.

51. A method according to claim 47, wherein the acrylonitrile polymer is a copolymer consisting of acrylonitrile, divinyl benzene and vinyl ethyl benzene shaped in the form of a fiber, a particle, a membrane or a hollow filament.

52. A method according to claim 44, wherein the enzyme is an oxidoreductase, hydrolase, transferase, lyase, isomerase or ligase and the substrate is a liquid medium comprising blood, urine, phospolipids, uric acid and glucose or a solution of a cephalosporin or penicillin compound.

53. A method according to claim 44, wherein said covalent bonding is effected directly through said crosslinking agent or condensing agent or through said crosslinking agent or condensing agent and through an intermediary spacer.

54. A method according to claim 53, wherein the crosslinking agent is glutaraldehyde.

55. A method according to claim 53, wherein the crosslinking agent is glutaraldehyde, crotonaldehyde, acrolein, hexamethylenediamine diisocyanate, hexamethylene-iso-thiocyanate, toluene diisocyanate, xylene diisocyanate, dimethyl adipiimidate, dimethyl suberiimidate, dimethyl-3,3'-dithio-bis-propionimidate or succinic acid anhydride.

56. A method according to claim 53, wherein the condensing agent is 1-ethyl-3-(3-dimethylaminopropyl)-carbodiimide.

57. A method according to claim 44, wherein the spacer is an alkylene diamine.

58. A process for preparation of 6-aminopenicillanic acid which comprises enzymatically deacylating a benzylpenicillin or alkaline salt thereof by using immobilized penicillin acylase bound to a carrier of water-insoluble acrylonitrile polymer containing from 20 μM to 1000 μM of amino groups per gram of the polymer, with the penicillin acylase bound by covalent bonding with a crosslinking agent or condensing agent in an inert medium, said polymer having a porous structure containing a number of micro-pores with an average size of 40 to 9000 Å, said acrylonitrile polymer being produced by effecting reduction of an acrylonitrile polymer having said porous structure in an inert non-solvent with lithium aluminum hydride.

59. A process according to claim 58, wherein the acrylonitrile polymer comprises polyacrylonitrile containing 90% or more of acrylonitrile shaped in the form of a fiber, a particle, a membrane or a hollow filament.

60. A process according to claim 58, wherein said penicillin acylase is an enzyme preparation obtained from cultured filtrate of penicillin acylase producing microorganisms.

61. A process according to claim 60, wherein the penicillin acylase producing microorganism is a strain belonging to genus Bacillus.

62. A process according to claim 61, wherein said strain is *Bacillus megaterium* B-400 (FERM-P 748).

63. A process according to claim 58, wherein said crosslinking agent is glutaraldehyde.

64. A process according to claim 58, wherein said micro-pores have an average size of 100 to 2000 Å.

65. A process for preparation of 7-amino-desacetoxy cephalosporanic acid which comprises enzymatically deacylating a 7-phenylacetamidodesacetoxy cephalosporanic acid by using immobilized acylase bound to a carrier of water-insoluble acrylonitrile polymer containing from 20 μM to 1000 μM of amino groups per gram of the polymer, with the acylase bound by covalent bonding with a crosslinking agent or condensing agent in an inert medium, said polymer having a porous structure containing a number of micro-pores with an average size of 40 to 9000 Å, said acrylonitrile polymer being produced by effecting reduction of an acrylonitrile polymer having said porous structure in an inert non-solvent with lithium aluminum hydride.

66. A process according to claim 65, wherein the acrylonitrile polymer comprises polyacrylonitrile containing 90% or more of acrylonitrile shaped in the form of a fiber, a particle, a membrane or a hollow filament.

67. A process according to claim 65, wherein said acylase is an enzyme preparation obtained from cultured filtrate of acylase producing microorganisms.

68. A process according to claim 67, wherein the acylase producing microorganism is a strain belonging to genus Bacillus.

69. A process according to claim 68, wherein said strain is *Bacillus megaterium* B-400 (FERM-P 748).

70. A process according to claim 65, wherein said crosslinking agent is glutaraldehyde.

71. A process according to claim 65, wherein said micropores have an average size of 100 to 2000 Å.

* * * * *